(12) United States Patent
Wiemer et al.

(10) Patent No.: US 7,902,228 B2
(45) Date of Patent: Mar. 8, 2011

(54) SCHWEINFURTHIN ANALOGUES

(75) Inventors: David F. Wiemer, Iowa City, IA (US); Jeffrey D. Neighbors, Iowa City, IA (US); John A. Beutler, Braddock, MD (US)

(73) Assignees: University of Iowa Research Foundation, Iowa City, IA (US); The United States of America, National Institute of Health, Washington, DC (US)

( * ) Notice: Subject to any disclaimer, the term of this patent is extended or adjusted under 35 U.S.C. 154(b) by 601 days.

(21) Appl. No.: 12/025,617

(22) Filed: Feb. 4, 2008

(65) Prior Publication Data
US 2008/0227852 A1 Sep. 18, 2008

Related U.S. Application Data

(63) Continuation of application No. 11/093,270, filed on Mar. 29, 2005, now Pat. No. 7,358,377.

(60) Provisional application No. 60/557,243, filed on Mar. 29, 2004.

(51) Int. Cl.
*A61K 31/4433* (2006.01)
*A61K 31/352* (2006.01)

(52) U.S. Cl. ......... 514/337; 514/100; 514/378; 514/397; 514/414; 514/454

(58) Field of Classification Search .................. 514/100, 514/337, 378, 397, 414, 454
See application file for complete search history.

(56) References Cited

U.S. PATENT DOCUMENTS
7,358,377 B2 4/2008 Wiemer et al.

OTHER PUBLICATIONS

International Search Report for International Application No. PCT/US2005/010482, mailed Mar. 30, 2006.
Beutler et al., "Schweinfurthin D, a cytotoxic stilbene from *Macaranga schweinfurthii*", Natural Product Letters, 14(5), 399-404 (2000).
Beutler, J. A. et al., "Cytotoxic Geranyl Stilbenes from *Macaranga schweinfurthii*", Journal of Natural Products, vol. 61, No. 12, 1509-1512, (1998).
Neighbors, JD et al., Synthesis of Nonracemic 3-Deoxyschweinfurthin B, J. Org. Chem., 70, 925-931. (2005).
Thoison, Odile et al., "Plants of New Caledonia. Part 140. Vedelianin, a hexahydroxanthene derivative isolated from *Macaranga vedeliana*", Phytochemistry, vol. 31, No. 4, 1439-1442, (1992).
Treadwell et al., "A cascade cyclization approach to schweinfurthin B", Organic Letters, 4(21), 3639-3642 (2002).
MSNBC News Service, "Mixed results on new cancer drug", Nov. 9, 2000.
Freshney, Culture of Animal Cells, A Manual of Basic Technique, Alan R. Liss, Inc., 1983, New York, p. 4.
Gura, Science, 278, 1041-1042 (1997).
Dermer, Bio/Technology, 12, 320 (1994).
MedicineNet.com, Definition of Cancer, 1 page, Aug. 29, 2006.
Thoison et al., "Vedelianin, a hexahydroxanthene derivative isolated from *Macaranga vedeliana*", Phytochemistry, 31(4), 1439-1442 (1992).

*Primary Examiner* — Bernard Dentz
(74) *Attorney, Agent, or Firm* — Viksnins Harris & Padys PLLP

(57) ABSTRACT

Methods and intermediates for preparing enantiomerically enriched Schweinfurthin analogs which are useful for the treatment of cancer, as well as novel Schweinfurthin analogs having anti-cancer activity, compositions comprising such analogs and therapeutic methods comprising administering such analogs.

21 Claims, 3 Drawing Sheets

SCHWEINFURTHIN ANALOGUES

RELATED APPLICATION

This application is a continuation of U.S. Ser. No. 11/093,270 filed on Mar. 29, 2005, now U.S. Pat. No. 7,358,377 which claims the benefit of United States Provisional Patent Application Number 60/557,243, filed 29 Mar. 2004; which applications are incorporated herein by reference and made a part hereof.

GOVERNMENT FUNDING

The invention described herein was made with government support under Grant Numbers DAMD17-01-1-0276 and DAMD17-02-1-0423 awarded by the US Department of Defense, Breast Cancer Research Program. The United States Government has certain rights in the invention.

BACKGROUND OF THE INVENTION

The family of natural products known as the schweinfurthins includes four compounds (FIG. 1, 1-4) isolated from the African plant *Macaranga schweinfurthii* Pax (see Beutler, J. A. et al., *J. Nat. Prod.* 1998, 61, 1509-1512; and Beutler, J. A., et al., *Nat. Prod. Lett.* 2000, 14, 349-404). Schweinfurthins A (1), B (2), and D (4) display significant activity in the NCI's 60-cell line anticancer assay with mean $GI_{50}$'s <1 μM. Their biological activity has attracted interest because some CNS, renal, and breast cancer cell lines are among the types most sensitive to these compounds. Inspection of the spectrum of activity shows no correlation with any currently used agents and suggests that these compounds may be acting at a previously unrecognized target or through a novel mechanism.

Repeated attempts to isolate larger samples of the schweinfurthins from natural sources have met with limited success; the absolute stereochemistry of these compounds has yet to be determined.

A cascade cyclization approach to the synthesis of racemic Schweinfurthin B was reported by E. Treadwell, et al., *Organic Letters*, 2002, 4, 3639-3642. The reported synthetic method, however, could not be elaborated to provide enantiomerically enriched mixtures of Schweinfurthin B.

Accordingly, there exists a need for synthetic methods that are useful for preparing enantiomerically enriched Schweinfurthin compounds. In addition to providing commercially useful quantities, such methods would allow sufficient quantities of the Schweinfurthin compounds to be prepared such that the absolute stereochemistry of the biologically active natural products can be determined. Additionally, general synthetic methods for preparing the Schweinfurthin ring structure would allow the preparation of structurally related compounds that might also have useful biological activity.

SUMMARY OF THE INVENTION

Applicant has discovered a process for preparing enantiomerically enriched Schweinfurthin B and D analogs. In one embodiment, the invention provides intermediate compounds useful for preparing Schweinfurthin analogs.

The invention also provides a compound of formula (XX):

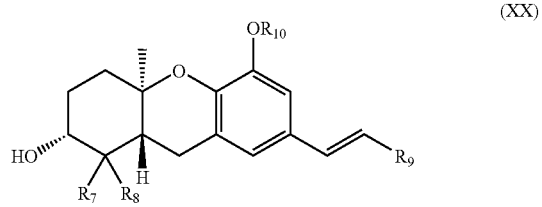

(XX)

wherein:

$R_7$ and $R_8$ are each independently H or $(C_1-C_6)$ alkyl;

$R_9$ is H, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, $(C_2-C_{15})$alkanoyloxy, aryl or heteroaryl, which aryl or heteroaryl is optionally substituted with one or more halo, hydroxy, cyano, $CF_3$, $OCF_3$, $NR^aR^b$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, $(C_1-C_{15})$alkoxy$(C_1-C_{15})$alkoxy, $-P(=O)(OH)_2$, and $(C_2-C_{15})$alkanoyloxy;

$R_{10}$ is H or $(C_1-C_6)$ alkyl; and $R^a$ and $R^b$ are each independently H or $(C_1-C_6)$alkyl wherein any $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy of $R_7$, $R_8$, and $R_9$ is optionally substituted with one or more halo, hydroxy, cyano, or oxo (=O).

or a pharmaceutically acceptable salt thereof.

The invention also provides a pharmaceutical composition comprising a compound of formula (XX), or a pharmaceutically acceptable salt thereof, in combination with a pharmaceutically acceptable diluent or carrier.

Additionally, the invention provides a therapeutic method for treating cancer comprising administering to a mammal in need of such therapy, an effective amount of a compound of formula (XX), or a pharmaceutically acceptable salt thereof.

The invention provides a compound of formula (XX) for use in medical therapy (e.g. for use in treating cancer), as well as the use of a compound of formula (XX) for the manufacture of a medicament useful for the treatment of cancer in a mammal, such as a human.

The invention also provides processes and intermediates disclosed herein that are useful for preparing compounds of formula (XX) as well as other Schweinfurthin analogs.

DETAILED DESCRIPTION

Figure 1:
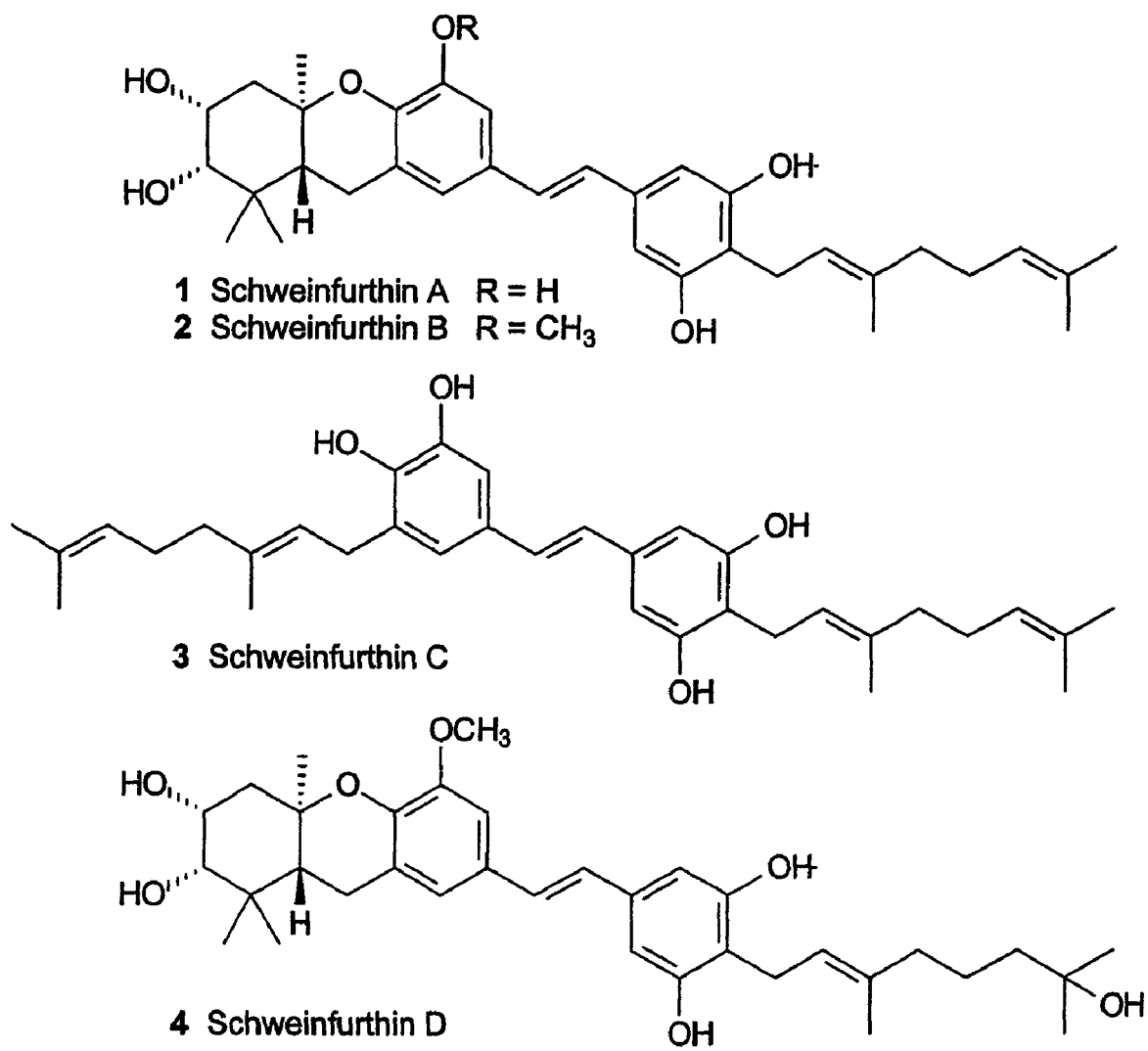
FIG. 1 shows the structure of Schweinfurthin analogs A-D.

The following definitions are used, unless otherwise described: alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Alkenyl denotes a hydrocarbon chain with one or more (1, 2, 3, or 4) double bonds. Likewise, alkynyl denotes a hydrocarbon chain with one or more (1, 2, 3, or 4) triple bonds. Aryl denotes a phenyl radical or an ortho-fused bicyclic carbocyclic radical having about nine to ten ring atoms in which at least one ring is aromatic; and heteroaryl encompasses a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The term "enantiomerically enriched" ("ee") as used herein refers to mixtures that have one enantiomer present to a greater extent than another. In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%.

The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "protecting group" or "blocking group" refers to any group which, when bound to a hydroxy prevents undesired reactions from occurring at this group and which can be removed by conventional chemical or enzymatic steps to reestablish the hydroxyl group. The particular removable blocking group employed is not critical and preferred removable hydroxyl blocking groups include conventional substituents such as allyl, benzyl, acetyl, chloroacetyl, thiobenzyl, benzylidine, phenacyl, methyl methoxy, silyl ethers (e.g., t-butyl-diphenylsilyl or t-butylsilyl ("TBS")) and any other group that can be introduced chemically onto a hydroxyl functionality and later selectively removed either by chemical or enzymatic methods in mild conditions compatible with the nature of the product. Suitable hydroxyl protecting groups are known to those skilled in the art and disclosed in more detail in T. W. Greene, *Protecting Groups In Organic Synthesis*; Wiley: New York, 1981, and the references cited therein.

Specific and preferred values listed below for radicals, substituents, and ranges, are for illustration only; they do not exclude other defined values or other values within defined ranges for the radicals and substituents.

Specifically, $(C_1-C_{15})$alkyl can be methyl, ethyl, propyl, isopropyl, butyl, iso-butyl, sec-butyl, t-butyl, pentyl, 3-pentyl, hexyl, heptyl, octyl, nonyl, decyl, do-decyl, hexadecyl, octadecyl, icosyl; $(C_1-C_{15})$alkoxy can be methoxy, ethoxy, propoxy, isopropoxy, butoxy, iso-butoxy, sec-butoxy, pentoxy, 3-pentoxy, or hexyloxy; $(C_2-C_{15})$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_{15})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_{15})$alkanoyl can be acetyl, propanoyl or butanoyl; $(C_1-C_{15})$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_{15})$alkanoyloxy can be acetoxy, propanoyloxy, butanoyloxy, isobutanoyloxy, pentanoyloxy, or hexanoyloxy; aryl can be phenyl, indenyl, or naphthyl.

In one specific embodiment of the invention $R_7$ is H.

In one specific embodiment of the invention $R_7$ is $(C_1-C_6)$alkyl.

In one specific embodiment of the invention $R_7$ is methyl.

In one specific embodiment of the invention % is H.

In one specific embodiment of the invention $R_8$ is $(C_1-C_6)$alkyl.

In one specific embodiment of the invention $R_8$ is methyl.

In one specific embodiment of the invention $R_9$ is H.

In one specific embodiment of the invention $R_9$ is $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, $(C_2-C_{15})$alkanoyloxy.

In one specific embodiment of the invention $R_9$ is $(C_1-C_{15})$alkyl, $(C_2-C_{15})$alkenyl, or $(C_2-C_{15})$alkynyl.

In one specific embodiment of the invention $R_9$ is aryl optionally substituted with one or more halo, hydroxy, cyano, $CF_3$, $OCF_3$, $NR^aR^b$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, and $(C_2-C_{15})$alkanoyloxy.

In one specific embodiment of the invention $R_9$ is aryl optionally substituted with one or more halo, hydroxy, cyano, $CF_3$, $OCF_3$, $NR^aR^b$, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, and $(C_2-C_{15})$alkanoyloxy.

In one specific embodiment of the invention $R_9$ is aryl optionally substituted with one or more halo, hydroxy, cyano, $CF_3$, $OCF_3$, $NR^aR^b$, $(C_2-C_{15})$alkenyl, $(C_1-C_{15})$alkoxy.

In one specific embodiment of the invention aryl is phenyl or naphthyl.

In one specific embodiment of the invention $R_9$ is of the formula

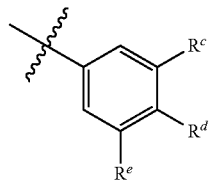

wherein:

$R^c$ and $R^d$ are each independently H, halo, hydroxy, $(C_1-C_{15})$alkyl, $(C_2-C_{15})$alkenyl, $(C_2-C_{15})$alkynyl, $(C_1-C_{15})$alkoxy, methoxymethoxy, and $(C_2-C_{15})$alkanoyloxy; and $R^d$ is H, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, and $(C_2-C_{15})$alkanoyloxy;

wherein any $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy of $R^c$, $R^e$, and $R^d$ is optionally substituted with one or more halo, hydroxy, cyano, or oxo (=O).

In one specific embodiment of the invention $R_9$ is of the formula

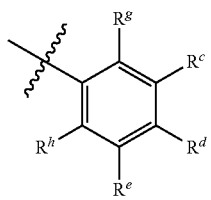

wherein:

$R^c$ and $R^e$ are each independently H, halo, hydroxy, $(C_1-C_{15})$alkyl, $(C_2-C_{15})$alkenyl, $(C_2-C_{15})$alkynyl, $(C_1-C_{15})$alkoxy, methoxymethoxy, and $(C_2-C_{15})$alkanoyloxy; and $R^d$ is H, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, and $(C_2-C_{15})$alkanoyloxy;

$R^g$ is H, cyano, fluoro, or —P(=O)(OH)$_2$; and $R^h$ is H, cyano, fluoro, or —P(=O)(OH)$_2$;

wherein any $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, or $(C_2-C_{15})$alkanoyloxy of $R^c$, $R^e$, and $R^d$ is optionally substituted with one or more halo, hydroxy, cyano, or oxo (=O).

In one specific embodiment of the invention $R^c$ and $R^e$ are each independently H, fluoro, chloro, bromo, hydroxy, or methoxy.

In one specific embodiment of the invention at least one of $R^c$ and $R^e$ is hydroxy.

In one specific embodiment of the invention $R^d$ is $(C_2-C_{15})$alkenyl optionally substituted with one or more halo, hydroxy, or oxo (=O).

In one specific embodiment of the invention $R^d$ is hydrogen, trans-3,7-dimethyl-2,6-octadien-1-yl, or trans-3,7-dimethyl-8-hydroxy-2,6-octadien-1-yl.

In one specific embodiment of the invention $R_9$ is isoxazolyl, imidazolyl, pyridyl, indolyl, or benzo[b]furanyl.

In one specific embodiment of the invention the compound of the invention is isolated and purified.

In one specific embodiment the invention provides a diol of formula (II)

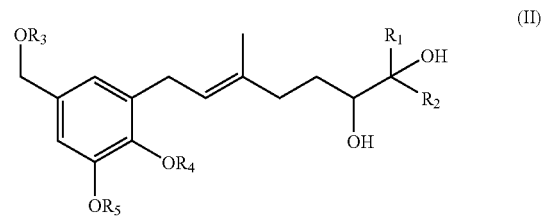

wherein $R_1$ and $R_2$ are each independently H or $(C_1-C_6)$alkyl; and $R_3$, $R_4$, and $R_5$ are each independently a suitable hydroxy protecting group.

In one specific embodiment the invention provides an epoxide of formula (III)

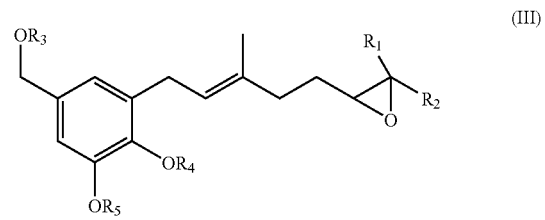

wherein $R_1$ and $R_2$ are each independently H or $(C_1-C_6)$alkyl; and $R_3$, $R_4$, and $R_5$ are each independently a suitable hydroxy protecting group.

In one specific embodiment the invention provides a compound of formula (IV)

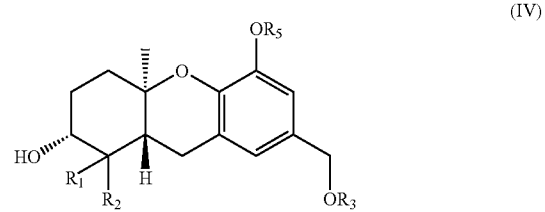

wherein $R_1$ and $R_2$ are each independently H or $(C_1-C_6)$ alkyl; and $R_3$ and $R_5$ are each independently a hydroxy protecting group.

In one specific embodiment the invention provides an alcohol of formula (V)

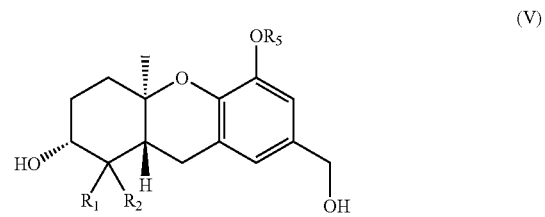

wherein $R_1$ and $R_2$ are each independently H or $(C_1-C_6)$ alkyl; and $R_5$ is a hydroxy protecting group.

In one specific embodiment the invention provides an aldehyde of formula (VI)

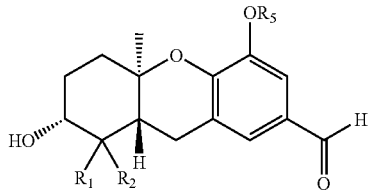

(VI)

wherein $R_1$ and $R_2$ are each independently H or $(C_1\text{-}C_6)$ alkyl; and $R_5$ is a hydroxy protecting group.

In one specific embodiment the invention provides a stilbene of formula (VII)

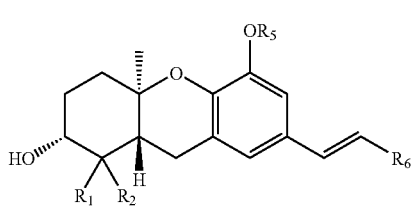

(VII)

wherein $R_1$ and $R_2$ are each independently H or $(C_1\text{-}C_6)$ alkyl;

$R_5$ is a hydroxy protecting group; and $R_6$ is aryl or heteroaryl optionally substituted with one or more halo, hydroxy, cyano, $CF_3$, $OCF_3$, $NR^aR^b$, $(C_1\text{-}C_{15})$ alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl, and $(C_2\text{-}C_{15})$alkanoyloxy; wherein any $(C_1\text{-}C_{15})$alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl, or $(C_2\text{-}C_{15})$alkanoyloxy of $R_6$ is optionally substituted with one or more halo, hydroxy, cyano, or oxo (=O);

In one specific embodiment the invention provides a compound of formula (VIII)

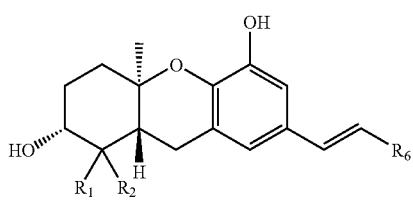

(VIII)

wherein $R_1$ and $R_2$ are each independently H or $(C_1\text{-}C_6)$ alkyl; and $R_6$ is aryl or heteroaryl optionally substituted with one or more halo, hydroxy, cyano, $CF_3$, $OCF_3$, $NR^aR^b$, $(C_1\text{-}C_{15})$ alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl, and $(C_2\text{-}C_{15})$alkanoyloxy; wherein any $(C_1\text{-}C_{15})$alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl, or $(C_2\text{-}C_{15})$alkanoyloxy of $R_6$ is optionally substituted with one or more halo, hydroxy, cyano, or oxo (=O).

In one specific embodiment the invention provides a diol of formula (IX)

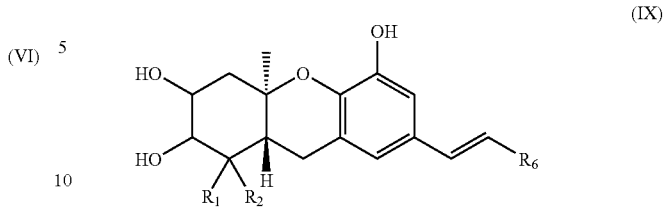

(IX)

wherein $R_1$ and $R_2$ are each independently H or $(C_1\text{-}C_6)$ alkyl; and $R_6$ is aryl or heteroaryl optionally substituted with one or more halo, hydroxy, cyano, $CF_3$, $OCF_3$, $NR^aR^b$, $(C_1\text{-}C_{15})$ alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl, and $(C_2\text{-}C_{15})$alkanoyloxy; wherein any $(C_1\text{-}C_{15})$alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl, or $(C_2\text{-}C_{15})$alkanoyloxy of $R_6$ is optionally substituted with one or more halo, hydroxy, cyano, or oxo (=O).

In one specific embodiment the invention provides a compound which is enantiomerically enriched and has an enantiomeric excess of at least about 90%.

In one specific embodiment the invention provides a compound which is enantiomerically enriched and has an enantiomeric excess of at least about 95%.

In one specific embodiment the invention provides a compound which is enantiomerically enriched and has an enantiomeric excess of at least about 98%.

In one specific embodiment the invention provides a compound which is enantiomerically enriched and has an enantiomeric excess of at least about 99%.

In one specific embodiment the invention provides a compound which is enantiomerically pure.

In one specific embodiment the invention provides a compound of formula (XX) which is the SSS enantiomer.

In one specific embodiment the invention provides a compound of formula (XX) which is the RRR enantiomer.

In one specific embodiment the invention provides a pharmaceutical composition comprising a compound of formula (XX), or a pharmaceutically acceptable salt thereof, and a pharmaceutically acceptable carrier.

In one specific embodiment the invention provides A method for treating cancer comprising administering a therapeutically effective amount of a compound of the invention to a mammal.

In one specific embodiment the invention provides a compound of the invention for use in medical therapy.

In one specific embodiment the invention provides the use of a compound as described in any one of claims 1-22 to prepare a medicament useful for treating cancer (e.g. breast cancer or a cancer of the CNS or renal system).

In one specific embodiment the invention provides method of preparing a compound of formula (IIa):

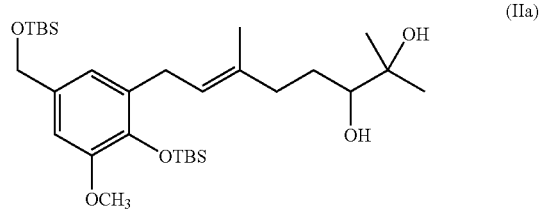

(IIa)

comprising oxidizing a diene of formula (Ia):

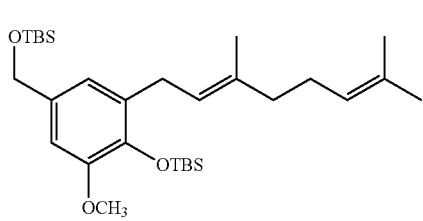
(Ia)

to provide the diol of formula (IIa).

In one specific embodiment the invention provides a method for preparing an epoxide of formula (IIIa)

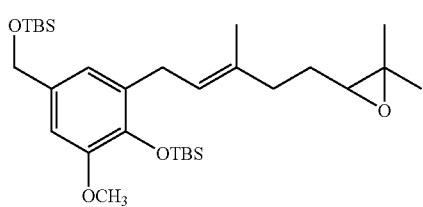
(IIIa)

comprising treating a diol of formula (IIa):

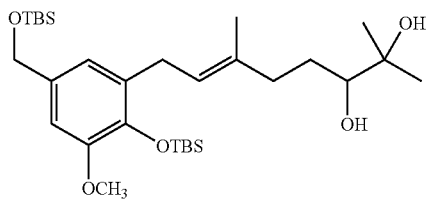
(IIa)

with a suitable base and mesyl chloride to provide the epoxide of formula (IIIa).

In one specific embodiment the invention provides a method of preparing a compound of formula (IVa)

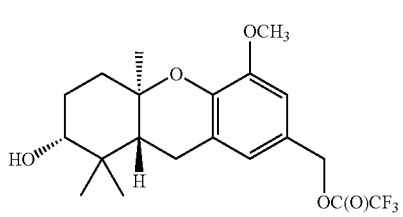
(IVa)

comprising treating epoxide of formula (IIIa):

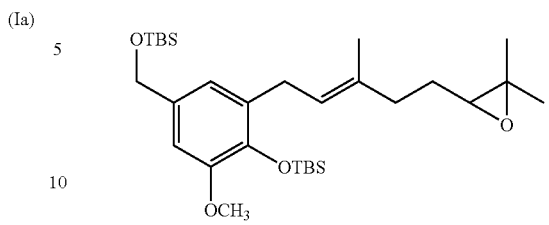
(IIIa)

with tetrabutylammonium fluoride and trifluoroacetic acid to provide a compound of formula (IVa).

In one specific embodiment the invention provides a method of preparing an alcohol of formula (Va)

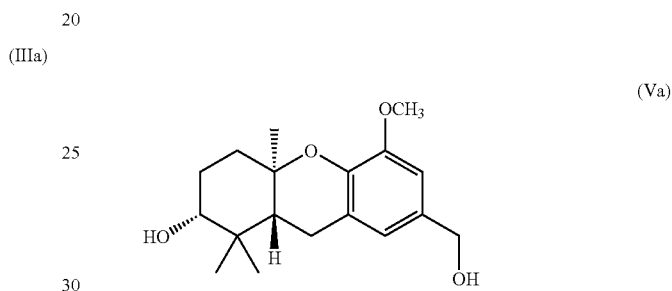
(Va)

comprising treating a compound of formula (IVa)

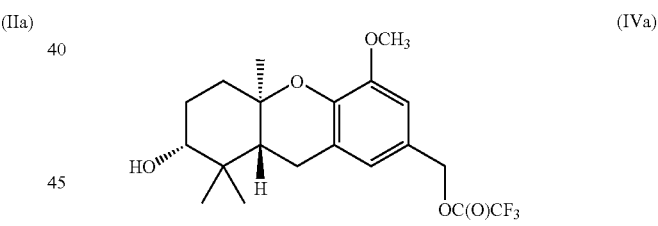
(IVa)

with potassium carbonate and methanol to provide the compound of formula (Va).

In one specific embodiment the invention provides a method of preparing an aldehyde of formula (VIa)

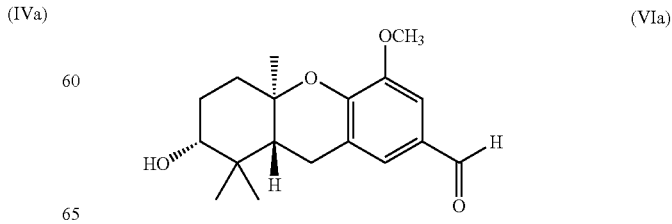
(VIa)

comprising oxidizing the alcohol of formula (Va)

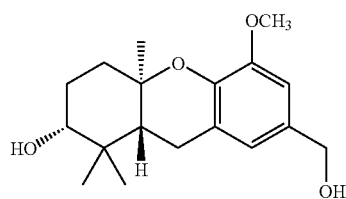
(Va)

to provide the aldehyde of formula (VIa).

In one specific embodiment the invention provides a method of preparing a stilbene of formula (VIIa):

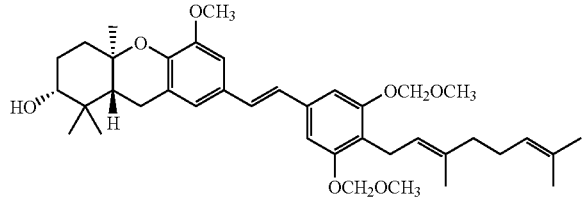
(VIIa)

comprising reacting an aldehyde of formula (VIa):

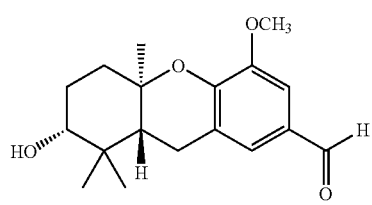
(VIa)

with a phosphonate of the following formula:

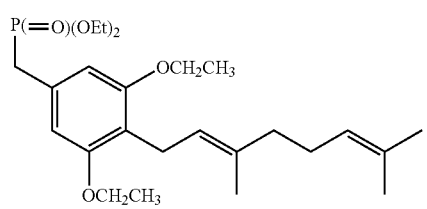

to provide the stilbene of formula (VIIa)

In one specific embodiment the invention provides a method for preparing a compound of formula (VIIIa):

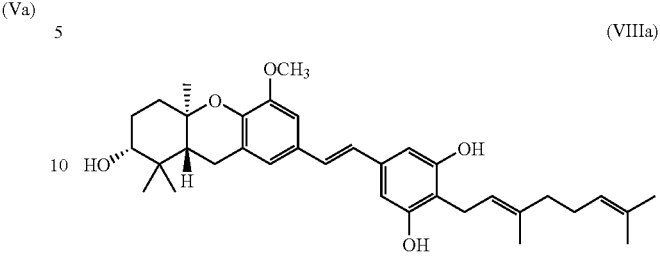
(VIIIa)

comprising deprotecting a corresponding compound of formula (VIIa):

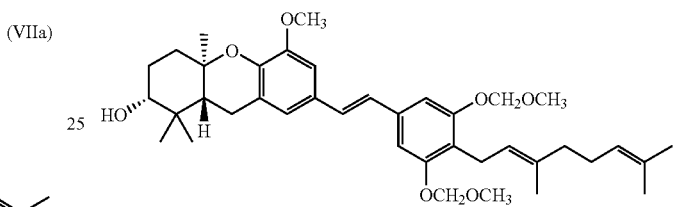
(VIIa)

by treatment with a suitable acid to provide the compound of formula (VIIIa).

In one specific embodiment the invention provides a method for preparing a diol compound of formula (IXa):

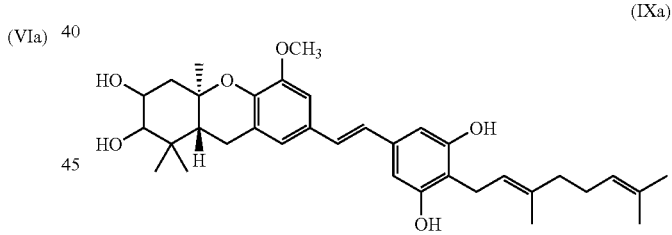
(IXa)

comprising converting a corresponding compound of formula (VIIIa)

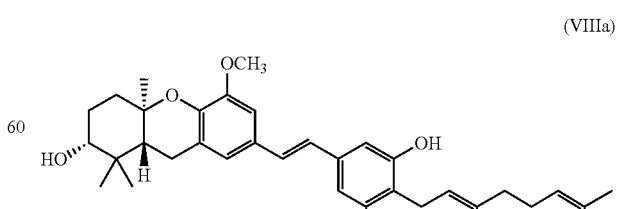
(VIIIa)

to the diol.

In one specific embodiment the invention provides a compound of formula (IIa):

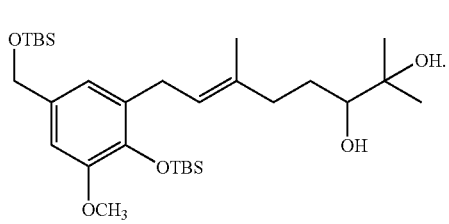

(IIa)

In one specific embodiment the invention provides an enantiomerically enriched compound of formula (IIIa):

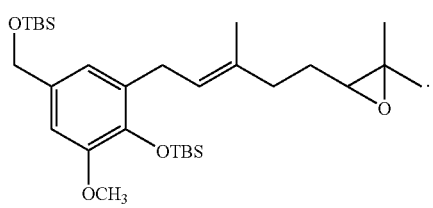

(IIIa)

In one specific embodiment the invention provides an enantiomerically enriched compound of the following formula:

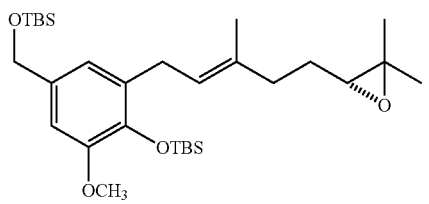

In one specific embodiment the invention provides a compound of formula (IVa)

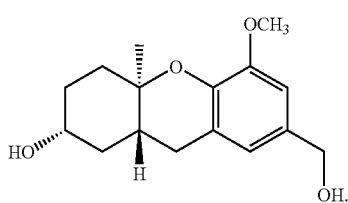

(IVa)

In one specific embodiment the invention provides a compound of formula (Va)

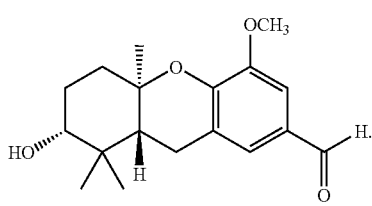

(Va)

In one specific embodiment the invention provides a compound of formula (VIa)

(VIa)

In one specific embodiment the invention provides a compound of formula (VIIa):

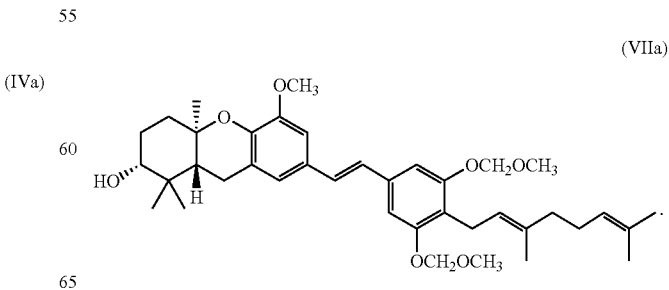

(VIIa)

In one specific embodiment the invention provides a compound of formula (VIIIa):

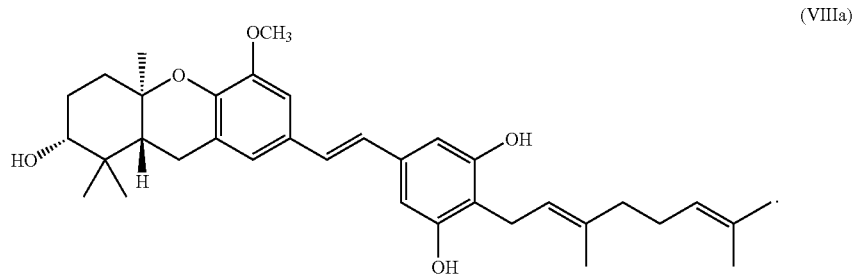

In one specific embodiment the invention provides a compound of formula (IXa):

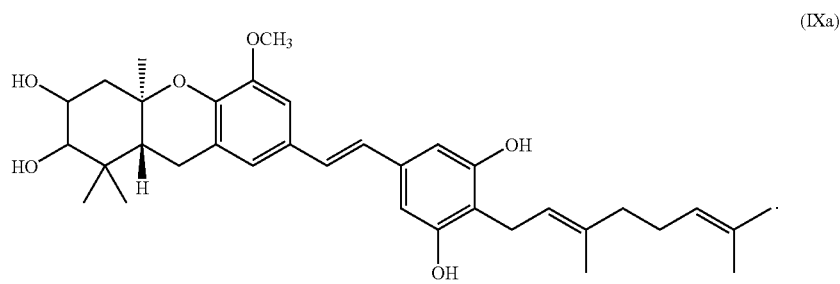

In one specific embodiment the invention provides a method of preparing a diol of formula (II);

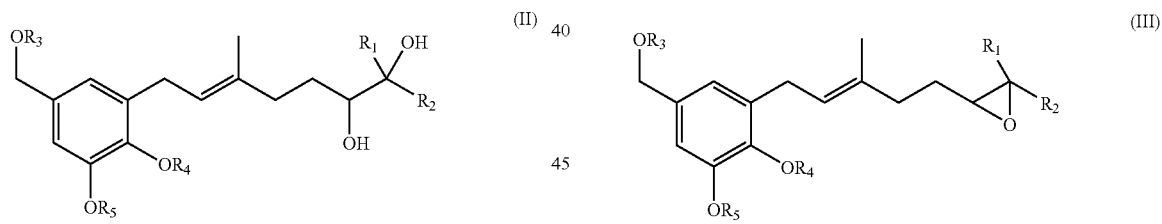

wherein $R_1$ and $R_2$ are each independently H or $(C_1\text{-}C_6)$alkyl; and $R_3$, $R_4$, and $R_5$ are each independently a suitable hydroxy protecting group; comprising: oxidizing a corresponding diene of formula (I);

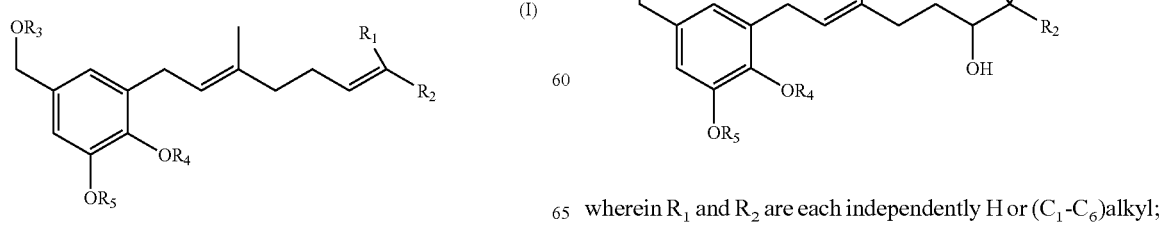

to provide the diol of formula (II).

In one specific embodiment the invention provides a method for preparing an epoxide of formula (III)

(III)

comprising converting a corresponding diol of formula (II);

(II)

wherein $R_1$ and $R_2$ are each independently H or $(C_1\text{-}C_6)$alkyl; and $R_3$, $R_4$, and $R_5$ are each independently a hydroxy protecting group; to the epoxide of formula (III).

In one specific embodiment the invention provides a method of preparing a compound of formula (IV)

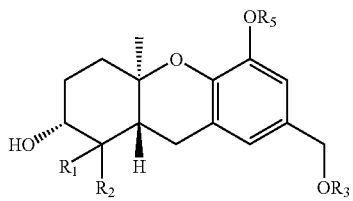
(IV)

comprising selectively removing $R_4$ from a corresponding epoxide of formula (III)

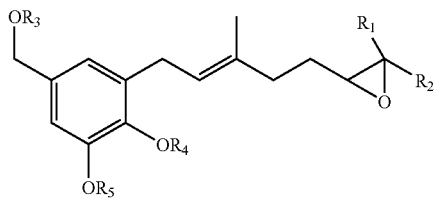
(III)

wherein $R_1$ and $R_2$ are each independently H or $(C_1\text{-}C_6)$alkyl; and $R_3$, $R_4$, and $R_5$ are each independently a hydroxy protecting group to provide an epoxy alcohol, and treating the epoxy alcohol with a suitable acid to provide a compound of formula (IV).

In one specific embodiment the invention provides a method of preparing an alcohol of formula (V)

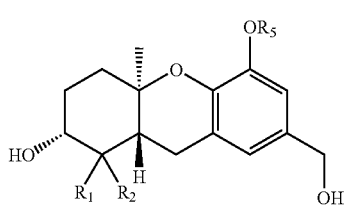
(V)

comprising selectively removing $R_3$ from a corresponding compound of formula (IV)

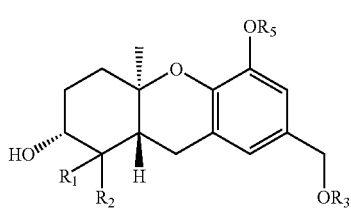
(IV)

wherein $R_1$ and $R_2$ are each independently H or $(C_1\text{-}C_6)$alkyl; and $R_3$ and $R_5$ are each independently a hydroxy protecting group.

In one specific embodiment the invention provides a method of preparing an aldehyde of formula (VI)

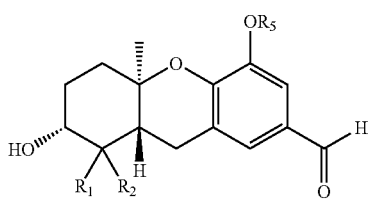
(VI)

comprising oxidizing a corresponding alcohol of formula (V)

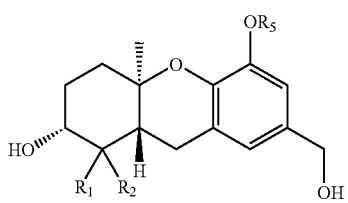
(V)

wherein $R_1$ and $R_2$ are each independently H or $(C_1\text{-}C_6)$alkyl; and $R_5$ is a hydroxy protecting group to provide the aldehyde of formula (VI).

In one specific embodiment the invention provides a method of preparing a stilbene of formula (VII):

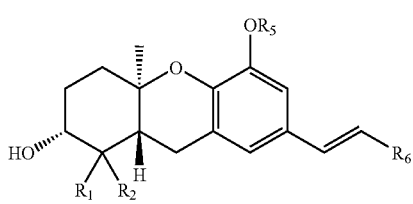
(VII)

wherein $R_6$ is aryl or heteroaryl optionally substituted with one or more halo, hydroxy, cyano, $CF_3$, $OCF_3$, $NR^aR^b$, $(C_1\text{-}C_{15})$alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl; or $(C_2\text{-}C_{15})$alkanoyloxy; wherein any $(C_1\text{-}C_{15})$alkyl, $(C_2\text{-}C_{15})$alkenyl, $(C_2\text{-}C_{15})$alkynyl, $(C_1\text{-}C_{15})$alkoxy, $(C_1\text{-}C_{15})$alkanoyl, $(C_1\text{-}C_{15})$alkoxycarbonyl, or $(C_2\text{-}C_{15})$alkanoyloxy of $R_6$ is optionally substituted with one or more halo, hydroxy, cyano, or oxo (=O); comprising reacting a corresponding aldehyde of formula (VI)

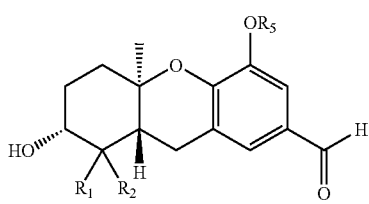
(VI)

wherein $R_1$ and $R_2$ are each independently H or $(C_1\text{-}C_6)$alkyl; and $R_5$ is a hydroxy protecting group with a requisite alkene forming reagent.

In one specific embodiment the invention provides a method for preparing a compound of formula (VIII):

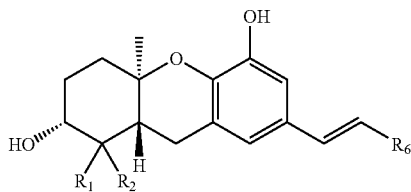

wherein $R_6$ is aryl or heteroaryl optionally substituted with one or more halo, hydroxy, cyano, $CF_3$, $OCF_3$, $NR^aR^b$, $(C_1$-$C_{15})$alkyl, $(C_2$-$C_{15})$alkenyl, $(C_2$-$C_{15})$alkynyl, $(C_1$-$C_{15})$alkoxy, $(C_1$-$C_{15})$alkanoyl, $(C_1$-$C_{15})$alkoxycarbonyl, or $(C_2$-$C_{15})$alkanoyloxy; wherein any $(C_1$-$C_{15})$alkyl, $(C_2$-$C_{15})$alkenyl, $(C_2$-$C_{15})$alkynyl, $(C_1$-$C_{15})$alkoxy, $(C_1$-$C_{15})$alkanoyl, $(C_1$-$C_{15})$alkoxycarbonyl, or $(C_2$-$C_{15})$alkanoyloxy of $R_6$ is optionally substituted with one or more halo, hydroxy, cyano, or oxo (=O); comprising removing the protecting group $R_5$ from a corresponding compound of formula (VII):

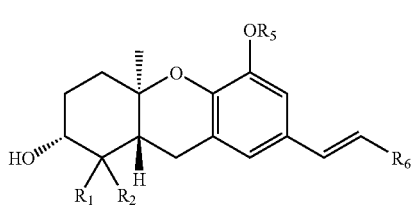

wherein $R_1$ and $R_2$ are each independently H or $(C_1$-$C_6)$alkyl; and $R_5$ is a hydroxy protecting group.

In one specific embodiment the invention provides a method for preparing a diol of formula (IX):

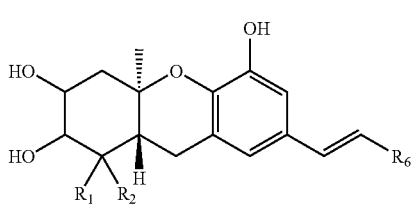

comprising converting a corresponding compound of formula (VIII):

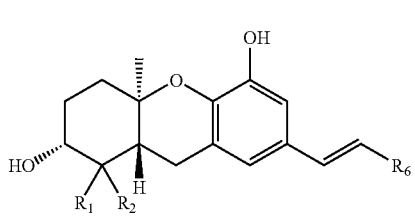

wherein $R_1$ and $R_2$ are each independently H or $(C_1$-$C_6)$alkyl; and $R_6$ is aryl or heteroaryl optionally substituted with one or more halo, hydroxy, cyano, $CF_3$, $OCF_3$, $NR^aR^b$, $(C_1$-$C_{15})$alkyl, $(C_2$-$C_{15})$alkenyl, $(C_2$-$C_{15})$alkynyl, $(C_1$-$C_{15})$alkoxy, $(C_1$-$C_{15})$alkanoyl, $(C_1$-$C_{15})$alkoxycarbonyl, or $(C_2$-$C_{15})$alkanoyloxy; wherein any $(C_1$-$C_{15})$alkyl, $(C_2$-$C_{15})$alkenyl, $(C_2$-$C_{15})$alkynyl, $(C_1$-$C_{15})$alkoxy, $(C_1$-$C_{15})$alkanoyl, $(C_1$-$C_{15})$alkoxycarbonyl, or $(C_2$-$C_{15})$alkanoyloxy of $R_6$ is optionally substituted with one or more halo, hydroxy, cyano, or oxo (=O); to the diol.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Suitable acids includes any organic acid suitable to catalyze the reaction, such as, trifluoroacetic acid (TFA). Suitable base includes any base suitable to catalyze the reaction, such as, triethyl amine (TEA).

Alkene forming reagent, as used herein, includes any reagent suitable to react with an aldehyde to form a double bond, such as, an ylide or phosphonate reagent.

As used herein, the terms "isolated" and "purified" refer to substances that are substantially free of other biological agents, for example, at least about 95%, about 98%, or about 99% pure.

As used herein, the term "AD-mix-α," refers to an asymmetric dihydroxylation chiral ligand system involving two naturally derived dihydroquinine (DHQD) alkaloid units linked together by a phthalazine (PHAL) linker. The enantiomeric alkaloid does not occur in nature, so the naturally derived diasteromeric dihydroquinidine (DHQ) based analogue is used, $(DHQ)_2PHAL$, $K_3Fe(CN)_6$— $K_2CO_3$ and $K_2OsO_4$-$2H_2O$ (First reported by K. Barry Sharpless (cf. J. Org. Chem., 1992, 57, 2768)). It is commercially available from Aldrich (licensed from Rhodia-Chirex Inc.) The term "AD-mix-α," includes the related reagent "AD-mix-β." Other suitable AD-mix-α reagents or alternatives are known to those skilled in the art and disclosed in more detail by Corey and Zhang in Organic Letters, 2001, 3, 3211-3214, and the references cited therein.

As used herein, the terms "treat," "treatment," and "treating," extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

Compounds and pharmaceutical compositions suitable for use in the present invention include those wherein the active compound is administered in an effective amount to achieve its intended purpose. More specifically, a "therapeutically effective amount" means an amount effective to treat the disease, disorder, and/or condition. Determination of a therapeutically effective amount is well within the capacity of persons skilled in the art, especially in light of the detailed disclosure provided herein.

The pharmaceutically active compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the pharmaceutically active compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the pharmaceutically active compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compounds of the invention can also be administered in combination with other therapeutic agents that are effective to treat cancer.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The anti-cancer activity of a compound of the invention may be determined using pharmacological models which are well known to the art, for example, NCI 60-cell line anticancer assay. Representative compounds of formula (XX) were tested and were found to have anti-cancer activity as illustrated in this assay.

The invention will now be illustrated by the following non-limiting Examples.

EXAMPLES

Figure 3:
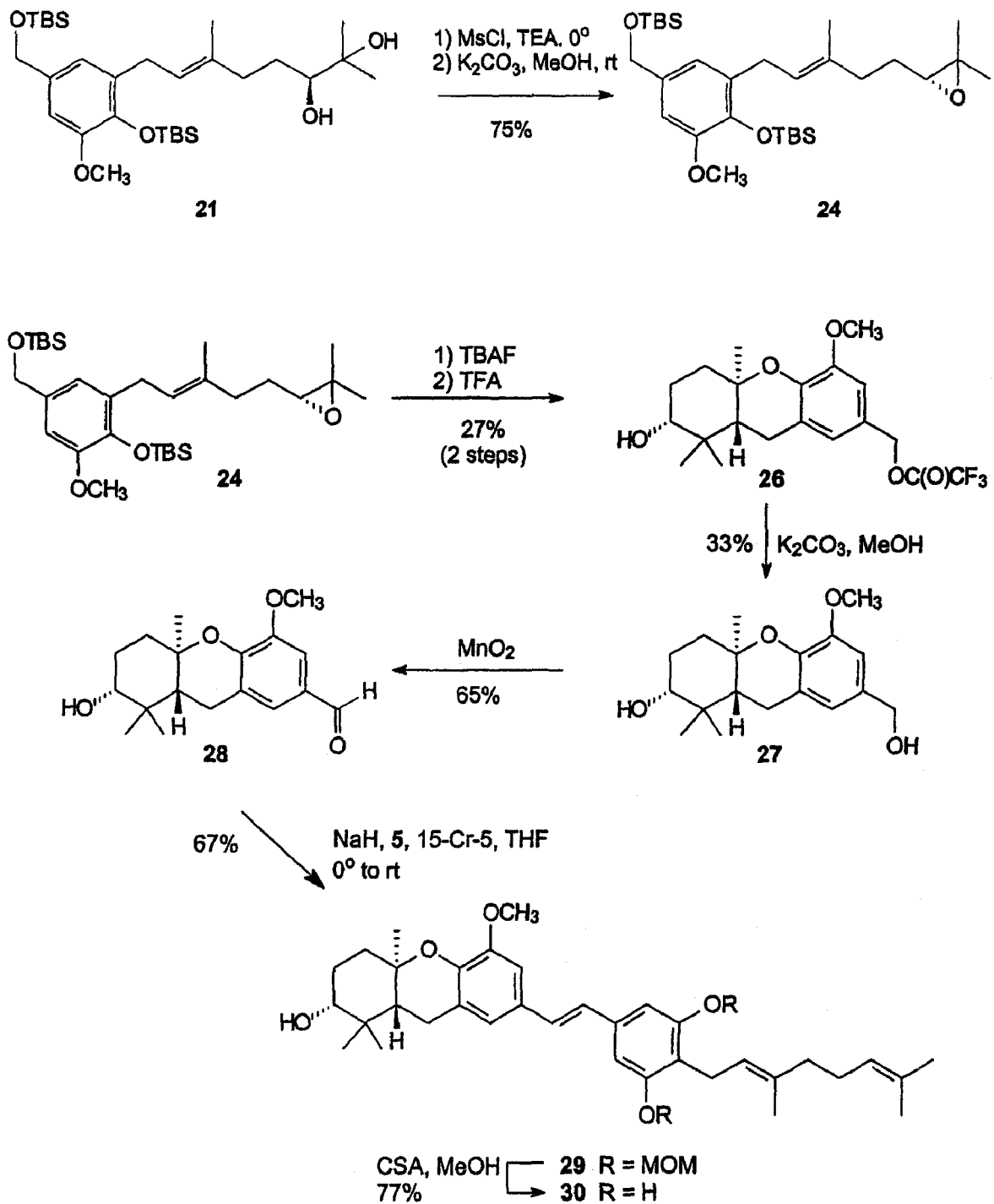

Example 1 3-Deoxyschweinfurthin B (30, FIG. 3)

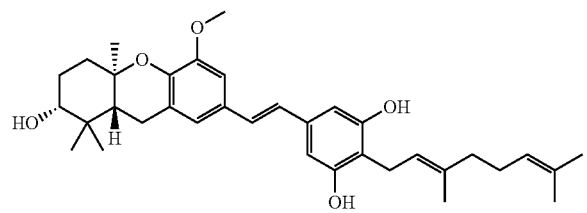

To a solution of stilbene 29 (24 mg, 0.04 mmol) in MeOH (2 mL) was added camphorsulphonic acid (10 mg, 0.04 mmol). The resulting solution was stirred at rt for 20 hr, and then heated to 60° C. for an additional 5 hr. The reaction was quenched by addition of sat. NaHCO$_3$, extracted with ethyl acetate, and the organic phase was washed with brine and dried over MgSO$_4$. Concentration in vacuo, followed by final purification by column chromatography (1:1, hexanes:ethyl acetate) afforded 3-deoxyschweinfurthin B (30, 16 mg, 79%) as a clear oil: $^1$H NMR (CDCl$_3$) δ 6.83 (m, 4H), 6.55 (s, 2H), 5.31 (s, 1H), 5.28 (t, J=6.9 Hz, 1H), 5.06 (m, 1H), 3.88 (s, 3H), 3.43 (m, 3H), 2.72 (d, J=9.1 Hz, 2H), 2.15-2.06 (m, 5H), 1.90-1.82 (m, 3H), 1.82 (s, 3H), 1.68 (s, 3H), 1.60 (s, 3H), 1.25 (s, 3H), 1.10 (s, 3H), 0.88 (s, 3H); $^{13}$C NMR (CDCl$_3$) δ 155.2 (2C), 148.9, 142.7, 139.2, 137.1, 132.1, 128.8, 128.6, 125.7, 124.2, 122.6, 121.4, 120.6, 112.8, 107.0, 106.2 (2C), 78.0, 77.1, 55.0, 46.8, 39.7, 38.4, 37.6, 28.3, 27.3, 26.4, 25.7, 23.1, 22.5, 19.8, 17.7, 16.2, 14.3; HRMS (ESI) calcd for C$_{35}$H$_{46}$O$_5$ (M$^+$) 546.3345, found 546.3342.

Figure 2:
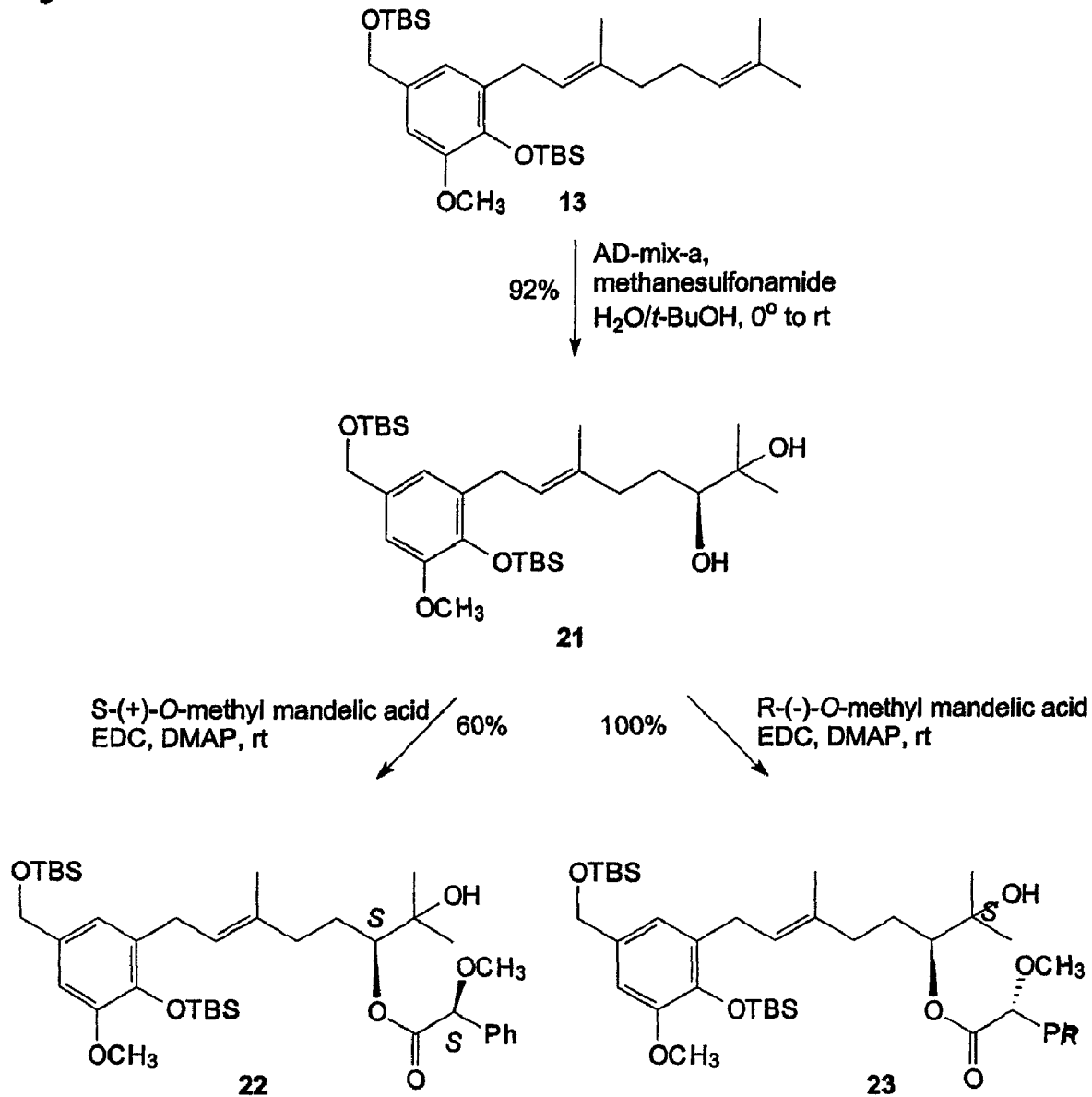
FIGS. 2-3 illustrates synthetic methods and intermediates useful for preparing Schweinfurthin analogs.

The intermediate stilbene 29 was prepared as follows.

a. 3-(3',7'-Dimethyl-2-octen-6'S,7'-diol)-4-(tert-butyldimethyl-siloxy)-5-methoxy-benzyloxy]-tert-butyldimethyl-silane (21, FIG. 2). To a solution of AD-mix-α (2.41 g) in water/t-BuOH (15 mL, 1:1) was added methanesulfonamide (0.17 g) and the solution was cooled to −7° C. The geranylated arene 13 (0.89 g, 1.71 mmol) (As reported by E. Treadwell, et al., *Organic Letters*, 2002, 4, 3639-3642.) was added via syringe as a neat oil and the solution was kept at 0° C. for 20 hours, and then allowed to warm to rt and stirred for an additional 5 days. Solid Na$_2$SO$_3$ was added and the solution was stirred for 1 hour. The solution was extracted with EtOAc, the resulting organic layer was washed with 2N NaOH and brine, and then dried (MgSO$_4$) and concentrated in vacuo to afford a clear oil. Final purification by column chromatography (1:1 hexanes:ethyl acetate) gave the diol 21 (0.86 g, 92%) as a clear oil: $^1$H NMR δ 6.72 (d, J=2.0 Hz, 1H), 6.65 (d, J=2.0 Hz, 1H), 5.38 (t, J=7.1 Hz, 1H), 4.64 (s, 2H), 3.77 (s, 3H), 3.35 (d, J=7.3 Hz, 2H), 3.35 (m, 1H), 2.33-2.23 (m, 2H), 2.17-2.00 (m, 2H), 1.70 (s, 3H), 1.66-1.56 (m, 1H), 1.50-1.36 (m, 1H), 1.19 (s, 3H), 1.15 (s, 3H), 1.00 (s, 9H), 0.93 (s, 9H), 0.17 (s, 6H), 0.08 (s, 6H); $^{13}$C NMR δ 149.7, 141.3, 135.7, 133.7, 132.1, 123.3, 119.0, 107.3, 78.2, 73.0, 65.0, 54.7, 36.7, 29.7, 28.5, 26.4, 26.1 (3C), 25.9 (3C), 23.2, 21.0, 18.9, 16.2, −3.9 (2C), −5.2 (2C). Anal. Calcd for C$_{30}$H$_{56}$O$_5$Si$_2$: C, 65.17; H, 10.21. Found: C, 65.11, H, 10.22.

b. 4-(tert-Butyldimethylsilyloxy)-5-methoxy-3-(3',7'-dimethyl-6'-epoxy-2'-octenyl)benzyloxy-tert-butyldimethyl-silane (24, FIG. 3). To a solution of diol 21 (2.03 g, 3.7 mmol), in CH$_2$Cl$_2$ (20 mL) at 0° C., was added TEA (1.35 mL, 9.69 mmol) followed 30 minutes later by MsCl (0.43 mL, 5.58 mmol). After 35 minutes the reaction was allowed to warm to rt, and after a total of 2 hrs a second aliquot of TEA (0.80 mL, 5.74 mmol) was added and the reaction was stirred for 30 min. A solution of K$_2$CO$_3$ (2.31 g, 16.7 mmol) in MeOH (70 mL) was poured into the vessel and the solution was allowed to react for 20 hours. After filtration and extraction of the of the resulting filtrate with ethyl acetate, the combined organic phase was washed with brine, dried (MgSO$_4$), and concentrated under vacuum to afford a white oil. Final purification by flash chromatography (12:1 hexanes:ethyl acetate) yielded the target epoxide 24 as a viscous clear oil (1.48 g, 75%): $^1$H NMR δ 6.72 (d, J=1.7 Hz, 1H), 6.65 (d, J=1.6 Hz, 1H), 5.36 (tm, J=7.2 Hz, 1H), 4.64 (s, 2H), 3.77 (s, 3H), 3.34 (d, J=7.1 Hz, 2H), 2.72 (t, J=6.3 Hz, 1H), 2.30-2.10 (m, 2H), 1.70 (s, 3H), 1.75-1.60 (m, 2H), 1.28 (s, 3H), 1.25 (s, 3H), 0.99 (s, 9H), 0.93 (s, 9H), 0.17 (s, 6H), 0.08 (s, 6H); $^{13}$C NMR δ 149.7, 141.3, 135.0, 133.7, 132.1, 123.3, 119.0, 107.3, 65.0, 64.2, 58.3, 54.7, 36.3, 28.5, 27.4, 26.1 (3C), 26.0 (3C), 24.9, 18.9, 18.7, 18.4, 16.2, −3.9 (2C), −5.2 (2C). Anal. Calcd for C$_{30}$H$_{54}$O$_4$Si$_2$: C, 67.36; H, 10.17. Found: C, 67.12; H, 10.28.

c. (6'R)-4-Hydroxy-3-methoxy-5-(3',7'-dimethyl-6'-epoxy-2'-octenyl)-benzyl alcohol (26, FIG. 3). Silyl ether 24 (840 mg, 1.57 mmol) was dissolved in THF (70 mL) and the solution was cooled to 0° C. To this solution was added TBAF (4.6 mL, 1.00 M in THF), the reaction was allowed to warm to rt and after 1.5 hrs was quenched with sat. NH$_4$Cl. After extraction with ethyl acetate, the combined organic extract was washed with water and brine, dried over MgSO$_4$, and concentrated in vacuo to give a yellow oil. Final purification by flash chromatography (4:1, hexanes:ethyl acetate) gave the diol 26 (352 mg, 96%): $^1$H NMR (CDCl$_3$) δ 6.77 (s, 1H), 6.74 (s, 1H), 5.70 (s, 1H), 5.37 (t, J=7.3 Hz, 1H), 4.57 (d, J=5.5 Hz, 2H), 3.89, (s, 3H), 3.36 (d, J=7.3 Hz, 2H), 2.71 (t, J=6.2 Hz, 1H), 2.24-2.12 (m, 2H), 1.74 (s, 3H), 1.68-1.62 (m, 3H), 1.27 (s, 3H), 1.25 (s, 3H); $^{13}$C NMR (CDCl$_3$) δ 146.3, 142.8, 135.3, 132.1, 127.0, 122.7, 120.7, 107.5, 65.6, 64.3, 58.4, 56.0, 36.4, 27.8, 27.3, 24.8, 18.7, 16.1. Anal. Calcd for C$_{18}$H$_{26}$O$_4$·0.5H$_2$O: C, 68.55; H, 8.63. Found: C, 68.23; H, 8.53.

d. Diol (27, FIG. 3). To a solution of epoxyphenol 26 (352 mg, 1.2 mmol) in CH$_2$Cl$_2$ (40 mL) at 0° C. was added trifluoroacetic acid (0.26 mL, 3.4 mmol). The resulting solution was allowed to stir 2 hours and Et$_3$N (1.4 mL, 10.0 mmol) was added. After an additional 30 minutes, water (75 mL) was added, the phases were separated, and the aqueous phase was extracted with ethyl acetate. The combined organic phase was washed with water, and brine then dried (MgSO$_4$), and concentrated. Final purification by flash chromatography (2:1 to 1:1 hexanes:ethyl acetate) afforded the tricyclic diol 27 (135 mg, 38%) as a light yellow oil: $^1$H NMR (CDCl$_3$) δ 6.73 (s, 1H), 6.70 (s, 1H), 4.57 (s, 2H), 3.86 (s, 3H), 3.39 (dd, J=11.6, 3.8 Hz, 1H), 2.69 (d, J=8.9 Hz, 2H), 2.15-2.04 (m, 2H), 1.88-1.59 (m, 6H, 2H exchange with D$_2$O), 1.23 (s, 3H), 1.08 (s, 3H), 0.87 (s, 3H); $^{13}$C NMR (CDCl$_3$) δ 148.9, 142.1, 132.0, 122.5, 120.4, 108.5, 78.0, 76.8, 65.5, 56.0, 46.7, 38.3, 37.6, 28.3, 27.3, 23.1, 19.7, 14.2; HRMS (ESI) calcd for C$_{18}$H$_{26}$O$_4$ (M$^+$) 306.1831, found 306.1823. Anal. Calcd for C$_{18}$H$_{26}$O$_4$.0.75H$_2$O: C, 67.58; H, 8.66. Found: C, 67.96; H, 8.33.

e. Aldehyde (28, FIG. 3). To a solution of benzylic alcohol 27 (251 mg, 0.82 mmol) in CH$_2$Cl$_2$ (30 mL) was added MnO$_2$ (1.71 g, 19.6 mmol) as a single aliquot. The resulting suspension was allowed to stir for 26 hours then filtered through celite and the residue was concentrated in vacuo to afford the aldehyde 28 as a white solid (249 mg, 100%): [α]$^{25.0}$$_D$=+97.8 (c 0.126, CHCl$_3$); $^1$H NMR (CDCl$_3$) δ 9.80 (s, 1H), 7.25 (s, 1H), 7.24 (s, 1H), 3.90 (s, 3H), 3.45 (dd, J=11.4, 3.8 Hz, 1H), 2.80-2.77 (m, 2H), 2.22-2.15 (m, 1H), 1.94-1.82 (m, 2H), 1.74-1.61 (m, 2H), 1.28 (s, 3H), 1.13 (s, 3H), 0.91 (s, 3H); $^{13}$C NMR δ 191.1, 149.5, 148.7, 128.7, 127.3, 122.5, 107.3, 78.4, 77.8, 56.0, 46.5, 38.4, 37.5, 28.2, 27.3, 23.0, 20.0, 14.3. Anal. Calcd for C$_{18}$H$_{24}$O$_4$.1H$_2$O: C, 67.06; H, 8.13. Found: C, 66.98; H, 8.17.

f. 3-Deoxy-dimethoxyschweinfurthin B (29, FIG. 3). A suspension of NaH (29 mg, 1.2 mmol), and 15-crown-5 (4 µL, 0.02 mmol) in THF (1.5 mL) was cooled to 5° C. To this was added aldehyde 28 (10 mg, 0.03 mmol) and phosphonate 5 (22 mg, 0.05 mmol) in THF (2 mL). The mixture was allowed to warm to rt and stirred a total of 18 hr. Water was added dropwise, and the solution was extracted with ether. The resulting organic phase was washed with brine, dried over MgSO$_4$, and concentrated in vacuo. Final purification by column chromatography (3.5:1 to 1:1, hexanes:ethyl acetate) gave the stilbene 29 (15.2 mg, 80%) as a straw colored oil: $^1$H NMR (CDCl$_3$) δ6.95-6.85 (m, 6H), 5.24 (s, 4H), 5.24 (t, 1H,), 5.07 (t, J=11.7 Hz, 1H), 3.89 (s, 3H), 3.50 (s, 6H), 3.40 (m, 3H), 2.72 (d, J=8.7 Hz, 2H), 2.16-1.85 (m, 7H), 1.79 (s, 3H), 1.70-1.65 (m, 3H), 1.65 (s, 3H), 1.57 (s, 3H), 1.26 (s, 3H), 1.10 (s, 3H), 0.89 (s, 3H); $^{13}$C NMR (CDCl$_3$) δ 155.9 (2C), 148.9, 142.5, 136.7, 134.6, 131.2, 128.9, 128.2, 126.4, 124.3, 122.6, 122.5, 120.5, 119.5, 106.8, 105.9 (2C), 94.5 (2C), 78.1, 77.0, 55.9 (2C), 55.9, 46.7, 39.8, 38.4, 37.7, 28.3, 27.3, 26.7, 25.6, 23.1, 22.7, 19.8, 17.6, 16.0, 14.3; HRMS (ESI) calcd for C$_{39}$H$_{54}$O$_7$ (M$^+$) 634.3870, found 634.3871. This compound is also a compound of the invention.

As shown in FIG. 2, the intermediate diol 21 can be prepared in enantiomerically pure form through formation of the S-mandelate or R-mandelate ester, followed by separation of the resulting diastereomers (e.g. by chromatography) and subsequent hydrolysis. For example see Neighbors J. D. et al., *J. Org. Chem.*, 2005, 70, 925-931. Details for the preparation of the mandelate esters is provided below.

g. S—O-methyl mandelate (22, FIG. 2). To a solution of diol 21 (33 mg, 0.1 mmol), EDC (19 mg, 0.1 mmol), and DAAP (4 mg, 0.03 mmol), in CH$_2$Cl$_2$ (2 mL) was added S-(+)-O-methyl mandelic acid (12 mg, 0.1 mmol). After 1 hour at rt, water was added and the resulting solution was extracted with CH$_2$Cl$_2$. The combined organic phase was dried (MgSO$_4$) and concentrated. Further purification by flash chromatography (5:1 to 2:1 hexanes:ethyl acetate) afforded the mandelate ester 22 (25 mg, 60%) as a clear oil, along with a small amount of the diastereomeric ester (not isolated): [α]$^{26.4}$$_D$=+42.1 (c 0.28, CHCl$_3$); $^1$H NMR (CDCl$_3$) δ 7.46 (dd, J=7.9, 1.8 Hz, 2H), 7.40-7.32 (m, 3H), 6.72 (s, 1H), 6.64 (s, 1H), 5.27 (t, J=8.0 Hz, 1H), 4.79 (s, 1H), 4.65 (s, 2H), 3.77 (s, 3H), 3.43 (s, 3H), 3.33 (d, J=7.9 Hz, 2H), 1.96 (t, J=8.0 Hz, 2H), 1.78-1.61 (m, 3H), 1.64 (s, 3H), 1.00 (s, 9H), 0.94 (s, 15H), 0.18 (s, 6H), 0.09 (s, 6H); $^{13}$C NMR δ 170.4, 149.7, 141.3, 136.5, 135.0, 133.7, 132.1, 129.0, 128.7 (2C), 127.2 (2C), 123.1, 119.0, 107.3, 82.6, 80.7, 72.3, 65.0, 57.3, 54.7, 35.0, 28.5, 28.1, 26.1 (3C), 26.0 (3C), 25.9, 24.6, 18.9, 18.4, 16.3, -3.9 (2C), -5.1 (2C); HRMS (ESI) calcd for C$_{39}$H$_{64}$O$_7$Si$_2$Na (M+Na)$^+$ 723.4088, found 723.4090.

h. R—O-methyl mandelate (23, FIG. 2). In a manner identical to that described above for preparation of ester 22, the diol 21 (38 mg, 0.07 mmol), EDC (20 mg, 0.1 mmol), and DMAP (10 mg, 0.08 mmol) were allowed to react with R-(–)—O-methyl mandelic acid (12 mg, 0.07 mmol). Standard workup and final purification by column chromatography (5:1 hexanes:ethyl acetate) afforded the target ester 23 (41.5 mg, 82%) as a clear oil along with the R,R-diastereomer (total yield of 100%). A diastereomeric ratio of 84:16, corresponding to an initial ee of 68%, was determined by integration of signals at 5.00 and 5.27 ppm in the $^1$H NMR spectrum of the initial mixture. For diastereomer 23: $^1$H NMR δ 7.46 (d, J=8.7 Hz, 2H), 7.36-7.28 (m, 3H), 6.73 (s, 1H), 6.57 (s, 1H), 5.00 (t, J=6.6 Hz, 1H), 4.80 (m, 2H), 4.65 (s, 2H), 3.78 (s, 3H), 3.43 (s, 3H), 3.24 (d, J=6.9 Hz, 2H), 1.60 (m, 5H, 1H exchanges with D$_2$O), 1.45 (s, 3H), 1.16 (s, 6H), 0.99 (s, 9H), 0.93 (s, 9H), 0.17 (s, 6H), 0.09 (s, 6H); $^{13}$C NMR δ 170.9, 149.7, 141.3, 136.3, 134.9, 133.6, 132.1, 128.8, 128.6 (2C), 127.1 (2C), 123.0, 119.0, 107.3, 82.7, 80.7, 72.4, 65.1, 57.3, 54.7, 35.4, 28.3, 28.2, 26.6, 26.1 (3C), 26.0 (3C), 24.7, 18.9, 18.4, 16.1, -3.9 (2C), -5.1 (2C); HRFABMS calcd for C$_{39}$H$_{64}$O$_7$NaSi$_2$ (M+Na)$^+$ 723.4088, found 723.4101.

Example 2

Dimethoxy-3-deoxyschweinfurthin B (34)

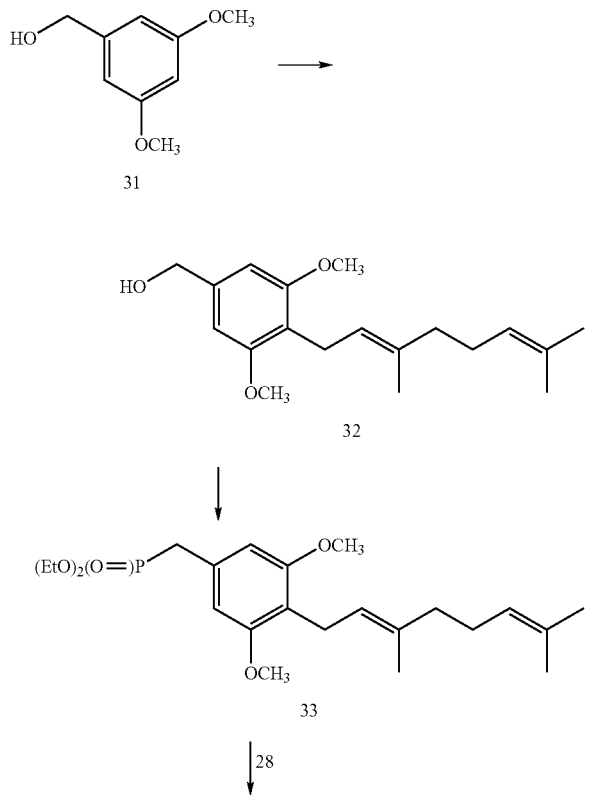

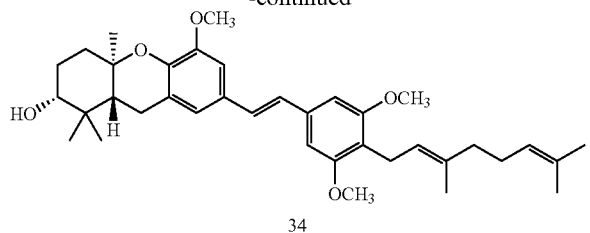

34

A solution of phosphonate 33 (20 mg, 0.04 mmol) and aldehyde 28 (10 mg, 0.03 mmol) in THF (1.5 mL) was added to a suspension of NaH (29 mg, 0.71 mmol, 60% suspension in oil) and 15C5 (4 µL, 22 nmol) in THF (2.5 mL) at 0° C. The resulting mixture was allowed to come to rt and stir for 20 hours. The solution was quenched with water, extracted (ether), and the combined organic layers were washed with brine. The residual organic layer was dried (MgSO$_4$), and concentrated in vacuo to give a yellow oil. Final purification by column chromatography (1:1 hexanes:EtOAc) afforded the target schweinfurthin analog 34 (6.4 mg, 37%) as a clear oil: $^1$H NMR δ 6.95-6.88 (m, 4H), 6.67 (s, 2H), 5.19 (t, J=6.8 Hz, 1H), 5.07 (t, J=5.7 Hz, 1H), 3.90 (s, 3H), 3.87 (s, 6H), 3.46-3.44 (m, 2H), 3.36-3.33 (m, 1H), 2.75-2.72 (m, 2H), 2.21-1.75 (m, 9H), 1.77 (s, 3H), 1.65 (s, 3H), 1.58 (s, 3H), 1.27 (s, 3H), 1.10 (s, 3H), 0.89 (s, 3H); HREIMS calcd for C$_{37}$H$_{50}$O$_5$ (M$^+$) 574.3658, found 574.3651.

The intermediate phosphonate 33 was prepared as follows.
a. [4-(3,7-Dimethyl-octa-2,6-dienyl)-3,5-dimethoxy-phenyl]-methanol (32) nBuLi (0.87 mL, 2.15 M in hexanes) was added dropwise to a solution of benzylic alcohol 31 (105 mg, 0.62 mmol) and TMEDA (0.28 mL, 1.9 mmol) in THF (10 mL) at −20° C. After the solution was stirred at −20° C. for 1 h, CuBr as its DMS complex (255 mg, 1.24 mmol) was added in one portion and the solution was stirred for 1 h at −20° C. Geranyl bromide (0.15 mL, 0.76 mmol) in THF (5 mL) was added via syringe and the reaction mixture was stirred for 2 h at −20° C. The reaction was quenched by addition of 1N NH$_4$Cl, the aqueous layer was neutralized to pH 7 with 1N HCl, and this layer was extracted with EtOAc. The combined organic layers were washed with brine, dried (MgSO$_4$), and concentrated in vacuo. Final purification of the residue by flash column chromatography (20% EtOAc in hexanes) afforded alcohol 32 (76 mg, 40%) as a clear oil. $^1$H NMR δ 6.54 (s, 2H), 5.17-5.12 (tm, J=7.1 Hz, 1H), 5.07-5.02 (tm, J=6.9 Hz, 1H), 4.63 (s, 2H), 3.80 (s, 6H), 3.31 (d, J=7 Hz, 2H), 2.04-1.89 (m, 4H), 1.74 (s, 3H), 1.63 (s, 3H), 1.55 (s, 3H); $^{13}$C NMR δ 160.3 (2C), 141.8, 136.8, 133.2, 126.6, 124.8, 119.9, 104.7 (2C), 68.0, 57.9 (2C), 41.9, 28.9, 27.8, 24.2, 19.8, 18.1. Anal. Calcd for C$_{19}$H$_{28}$O$_3$: C, 74.96; H, 9.27. Found: C, 74.82; H, 9.34.
b. [4-(3,7-dimethyl-octa-2,6-dienyl)-3,5-dimethoxy-benzyl]-phosphonic acid diethyl ester (33) Methanesulfonyl chloride (0.15 mL, 1.94 mmol) was added dropwise to a solution of alcohol 32 (181 mg, 0.59 mmol) and Et$_3$N (0.3 mL 1.9 mmol) in CH$_2$Cl$_2$ (5 mL) and the solution was stirred for 2 h at 0° C. The reaction mixture was allowed to warm to rt over 5 h, quenched by addition of H$_2$O, and extracted with EtOAc. The combined organic layers were washed with NH$_4$Cl (sat), brine, dried (MgSO$_4$), and concentrated in vacuo. The resulting residue and NaI (310 mg, 2.06 mmol) were stirred in acetone (8 mL) for 24 h. The reaction mixture was concentrated in vacuo to afford a red solid, which was dissolved in EtOAc. After the resulting yellow solution was washed once with NaHCO$_3$ and then with Na$_2$S$_2$O$_3$ until the color faded, it was extracted with ether and the combined organic layers were dried (MgSO$_4$) and concentrated in vacuo. The resulting yellow oil was added to triethyl phosphite (1.5 mL) and the mixture was heated at 100° C. for 20 h. After the solution was allowed to cool to rt, it was poured into ether (5 mL). The mixture was extracted with ether, dried (MgSO$_4$), and concentrated in vacuo. The initial yellow oil was purified by flash chromatography (50% EtOAc in hexanes) to afford phosphonate 33 (73 mg, 40%) as a light yellow oil: $^1$H NMR δ 6.49 (d, J=2.4 Hz, 2H), 5.18-5.13 (tm, J=7.3 Hz, 1H), 5.07-5.02 (tm, J=6.8 Hz, 1H), 4.09-3.98 (m, 4H), 3.80 (s, 6H), 3.31 (d, J=7.0 Hz, 2H), 3.11 (d, J$_{PH}$=21.5 Hz, 2H), 2.06-1.94 (m, 4H), 1.82 (s, 3H), 1.68 (s, 3H), 1.56 (s, 3H), 1.27 (tm, J=7.0 Hz, 6H); $^{13}$C NMR δ 160.9 (d, J$_{CP}$=3.1 Hz, 2C), 137.5, 134.1, 132.9 (d, J$_{CP}$=9.0 Hz), 127.5, 125.7 (d, J$_{CP}$=2.9 Hz), 120.1 (d, J$_{CP}$=3.4 Hz), 108.6 (d, J$_{CP}$=6.7 Hz, 2C), 65.1 (d, J$_{CP}$=6.7 Hz, 2C), 58.7 (2C), 42.8, 37.1 (d, J$_{CP}$=137.3 Hz), 29.7, 28.6, 24.9, 20.6, 19.4 (d, J$_{CP}$=6.0 Hz, 2C), 18.9; $^{31}$P NMR δ +26.4; HRMS (EI) calcd for C$_{23}$H$_{37}$O$_5$PNa [M$^+$+Na], 447.2276; found 447.2265.

Example 3 7-{2-[4-(3,7-Dimethyl-octa-6,7-dienyl)-phenyl]-vinyl}-5-methoxy-1,1,4a-trimethyl-2,3,4,4a,9,9a-hexahydro-1H-xanthen-2-ol (56)

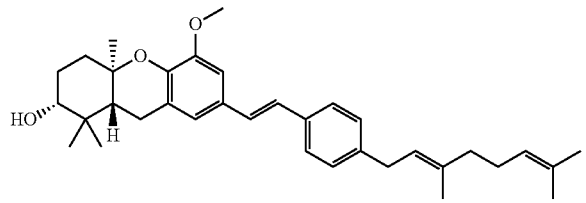

To a suspension of NaH (64 mg, 1.6 mmol, 60% in mineral oil) in THF (17 mL) at 0° C. was added a mixture of phosphonate 43 (56 mg, 0.15 mmol) and aldehyde 28 (28 mg, 0.09 mmol) in THF (3 mL). After 5 min 15C5 (10 µL) was added and the reaction was allowed to warm to rt and stir for 19 hr. Water was added and the mixture was extracted with ethyl acetate. The combined organic phase was washed with brine and dried (MgSO$_4$). Concentration in vacuo afforded a yellow oil and final purification by column chromatography (1:1 hexanes:EtOAc) gave the stilbene 56 (26 mg, 55%) as a clear oil: $^1$H NMR δ 7.40 (m, 2H), 7.16 (m, 2H), 6.95-6.94 (m, 2H), 6.89-6.88 (m, 2H), 5.34 (td, J=7.3, 1.0 Hz, 1H), 5.11 (t, J=6.7 Hz, 1H), 3.89 (s, 3H), 3.43 (dd, J=11.7, 4.0 Hz, 1H), 3.35 (d, J=7.3 Hz, 2H), 2.74-2.71 (m, 2H), 2.16-2.04 (m, 5H), 1.90-1.81 (m, 2H), 1.80-1.70 (m, 2H), 1.71 (s, 3H), 1.69 (s, 3H), 1.61 (s, 3H), 1.25 (s, 3H), 1.10 (s, 3H), 0.90 (s, 3H); $^{13}$C NMR δ 148.9, 142.5, 140.9, 136.3, 135.2, 131.4, 129.1 (2C), 128.6, 127.8, 126.2, 126.2 (2C), 124.2, 122.8, 122.6, 120.4, 106.9, 78.0, 77.0, 56.0, 46.7, 39.7, 38.4, 37.6, 33.9, 28.3, 27.3, 26.6, 25.7, 23.1, 19.8, 17.7, 16.1, 14.3; HREIMS calcd for C$_{35}$H$_{46}$O$_3$ (M$^+$) 514.3447, found 514.3447.

The intermediate phosphonate 43 was prepared as follows.

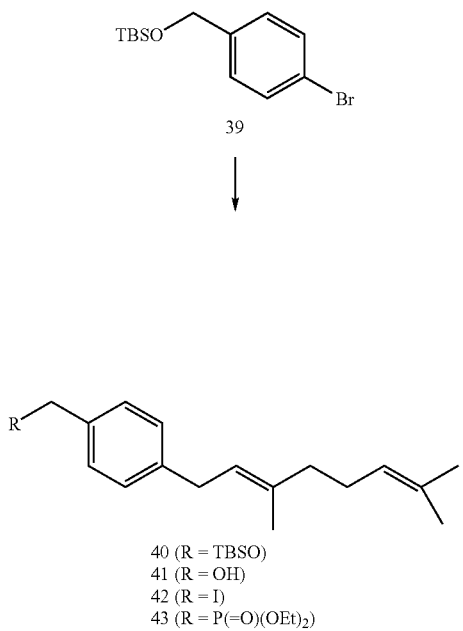

40 (R = TBSO)
41 (R = OH)
42 (R = I)
43 (R = P(=O)(OEt)$_2$)

a. tert-Butyl-[4-(3,7-dimethyl-octa-2,6-dienyl)-benzyloxy]-dimethyl-silane (40) nBuLi (7.90 mL, 2.5 M in hexane, 19.8 mmol) was added dropwise to a stirred solution of aryl bromide 39 (3.13 g, 10.4 mmol) in THF (15 mL) over 15 min at −78° C. The reaction mixture was allowed to stir for 2 h at −78° C. Geranyl bromide (2.5 mL, 12.6 mmol) was added dropwise and the reaction mixture was stirred for 2 h at −78° C. The reaction mixture was allowed to warm to rt, was quenched by addition of H$_2$O, and then was extracted with ether. The combined organic layers were washed with NH$_4$Cl (sat), brine, dried (MgS$_4$), and concentrated in vacuo. Final purification of the residue by flash column chromatography (hexanes) afforded compound 40 (2.61 g, 70%) as a light yellow oil: $^1$H NMR δ 7.24-7.19 (m, 2H), 7.14-7.12 (m, 2H), 5.43-5.38 (tm, J=7.4 Hz, 1H), 5.20-5.15 (tm, J=7.5 Hz, 1H), 4.77 (s, 2H), 3.41 (d, J=7.4 Hz, 2H), 2.19-2.09 (m, 4H), 1.77 (s, 3H), 1.75 (s, 3H), 1.67 (s, 3H), 1.01 (s, 9H), 0.16 (s, 6H); $^{13}$C NMR δ. 140.6, 140.0, 136.3, 131.6, 128.4 (2C), 126.4 (2C), 124.5, 123.4, 65.1, 39.9, 34.1, 26.8, 26.2 (3C), 25.9, 18.6, 17.9, 16.3, −5.0 (2C). Anal. Calcd for C$_{23}$H$_{38}$OSi: C, 77.01; H, 10.68. Found: C, 77.08; H, 10.69.

b. [4-(3,7-Dimethyl-octa-2,6-dienyl)-phenyl]-methanol (41) TBAF (26.0 mL, 1.0 M in THF, 26.0 mmol) was added dropwise to a stirred solution of protected alcohol 40 (2.56 g, 7.14 mmol) in THF (20 mL). The solution was stirred for 2 h at 0° C. and then was allowed to warm to rt over 5 h. The reaction was quenched by addition of NH$_4$Cl (sat), and extracted with EtOAc. The combined organic layers were washed with brine, dried (MgSO$_4$), and concentrated in vacuo. Final purification of the residue by flash column chromatography (20% EtOAc in hexanes) afforded compound 41 (1.35 g, 77%) as a light yellow oil: $^1$H NMR δ 7.28-7.24 (m, 2H), 7.18-7.15 (m, 2H), 5.35-5.30 (tm, J=7.2 Hz, 1H), 5.12-5.08 (tm, J=6.7 Hz, 1H), 4.63 (s, 2H), 3.35 (d, J=7.3 Hz, 2H), 2.12-2.02 (m, 4H), 1.70 (s, 1H exchanges with D$_2$O), 1.70 (s, 3H), 1.68 (s, 3H), 1.60 (s, 3H); $^{13}$C NMR δ 141.6, 138.5, 136.5, 131.7, 128.7 (2C), 127.4 (2C), 124.4, 123.1, 65.4, 39.9, 34.1, 26.8, 26.0, 17.9, 16.3; HRMS (EI) calcd for C$_{17}$H$_{24}$O [M$^+$], 244.1827; found 244.1832.

c. 1-(3,7-Dimethyl-octa-2,6-dienyl)-4-iodomethyl-benzene (42) Methanesulfonyl chloride (1.8 mL, 23.3 mmol) was added dropwise to a stirred solution of alcohol 41 (1.27 g, 5.22 mmol) and Et$_3$N (3 mL 21.5 mmol) in CH$_2$Cl$_2$ (20 mL) at 0° C. over 2 h. The reaction mixture was allowed to warm to rt over 5 h. After the reaction was quenched by addition of water, it was extracted with EtOAc. The combined organic layers were washed with NH$_4$Cl (sat), brine, dried (MgSO$_4$), and concentrated in vacuo. The resulting yellow residue was treated with NaI (3.51 g, 23.4 mmol) in acetone (20 mL) at rt for 24 h. The reaction mixture was concentrated in vacuo to afford a red solid, which was dissolved in EtOAc. After the resulting solution was washed once with NaHCO$_3$ and then with Na$_2$S$_2$O$_3$ until the color faded, the aqueous layer was extracted with ether and the combined organic layers were dried (MgSO$_4$) and concentrated in vacuo. Final purification of the residue by flash column chromatography (20% EtOAc in hexanes) afforded compound 42 (1.44 g, 78%) as a yellow oil: $^1$H NMR δ 7.30-7.24 (m, 2H), 7.11-7.08 (m, 2H), 5.35-5.30 (tin, J=7.2 Hz, 1H), 5.14-5.09 (tin, J=6.6 Hz, 1H), 4.47 (s, 2H), 3.33 (d, J=7.2 Hz, 2H), 2.14-2.03 (m, 4H), 1.71 (s, 6H), 1.61 (s, 3H); $^{13}$C NMR δ. 141.9 (2C), 136.8, 131.7, 129.0 (2C), 128.9 (2C), 124.4, 122.8, 39.9, 34.1, 26.8, 26.0, 17.9, 16.3, 6.4; HRMS (EI) calcd for C$_{17}$H$_{23}$ [M$^+$−I], 227.1800; found 227.1801.

d. Diethyl[4-(3,7-dimethyl-octa-2,6-dienyl)-benzyl]phosphonate (43)

A stirred solution of iodide 42 (1.35 g, 3.82 mmol) in triethyl phosphite (25 mL) was heated at reflux for 4 h, and then allowed to cool to rt. Excess triethyl phosphite was removed by vacuum distillation and the resulting yellow oil was purified by flash chromatography (30% EtOAc in hexanes) to afford phosphonate 43 (1.34 g, 97%) as a light yellow oil: $^1$H NMR δ 7.22-7.18 (m, 2H), 7.12-7.09 (m, 2H), 5.33-5.29 (tm, J=7.2 Hz, 1H), 5.11-5.08 (tm, J=6.6 Hz, 1H), 4.06-4.00 (m, 4H), 3.32 (d, J=7.2 Hz, 2H), 3.11 (d, J$_{PH}$=21.3 Hz, 2H), 2.12-2.05 (m, 4H), 1.69 (s, 3H), 1.68 (s, 3H), 1.60 (s, 3H), 1.24 (t, J=7.2 Hz, 6H); $^{13}$C NMR δ 140.6 (d, J$_{CP}$=3.8 Hz), 136.5, 131.7, 129.8 (d, J$_{CP}$=6.5 Hz, 2C), 128.9 (d, J$_{CP}$=9.3 Hz), 128.7 (d, J$_{CP}$=3.1 Hz, 2C), 124.5, 123.1, 62.2 (d, J$_{CP}$=6.8 Hz, 2C), 39.9, 34.4, 32.6 (d, J$_{CP}$=138.2 Hz), 26.8, 26.0, 17.9, 16.6 (d, J$_{CP}$=6.1 Hz, 2C), 16.3; $^{31}$P NMR δ +26.6. Anal. Calcd for C$_{21}$H$_{33}$O$_3$P: C, 69.21; H, 9.13. Found: C, 69.09; H, 9.16.

Example 4

7-{2-[4-(3,7-Dimethyl-octa-2,6-dienyl)-3,5-difluoro-phenyl]-vinyl}-5-methoxy-1,1,4a-trimethyl-2,3,4,4a, 9,9a-hexahydro-1H-xanthen-2-ol (57)

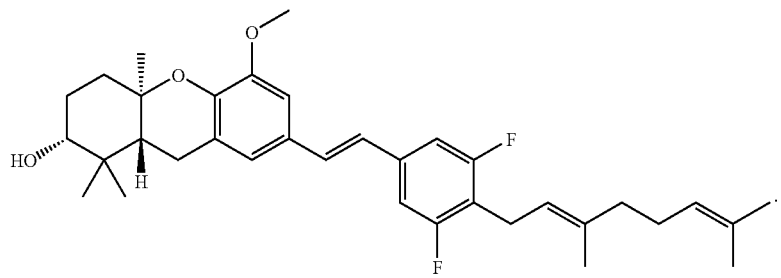

To a stirred suspension of NaH (30 mg, 1.3 mmol) and 15C5 (5 μL, 3 mol %) in THF (5 mL) was added phosphonate 46 (71 mg, 0.177 mmol) and aldehyde 28 (20 mg, 0.066 mmol) at 0° C. and the solution was allowed to warm to rt over 10 h. The reaction was quenched by addition of water and then was extracted with EtOAc. The combined organic layers were washed with brine, dried (MgSO$_4$), and concentrated in vacuo. Final purification of the residue by flash column chromatography (50% EtOAc in hexanes) afforded compound 57 (30.9 mg, 85%) as a clear oil: $^1$H NMR δ 6.99-6.79 (m, 6H), 5.26-5.22 (tm, J=7.0 Hz, 1H), 5.09-5.04 (tm, J=6.8 Hz, 1H), 3.9 (s, 3H), 3.47-3.42 (m, 1H), 3.37-3.35 (dm, J=7.2 Hz, 2H), 2.77-2.74 (m, 1H), 2.73-2.70 (m, 1H), 2.18-1.82 (m, 7H), 1.76 (s, 3H), 1.72-1.69 (m, 2H), 1.65 (s, 3H), 1.58 (s, 3H), 1.27 (s, 3H), 1.09 (s, 3H), 0.90 (s, 3H); $^{13}$C NMR δ 163.4-160.0 (dd, J$_{CF}$=241.8 Hz, J$_{CF}$=9.8 Hz, 2C), 149.3, 143.4, 137.9, 136.8, 131.7, 130.5, 124.5 (t, J$_{CF}$=9.5 Hz), 124.3, 123.0, 121.1, 120.8, 115.9 (t, J$_{CF}$=23.4 Hz), 110.0, 108.7 (dd, J$_{CF}$=26.6 Hz, J$_{CF}$=8.6 Hz, 2C), 107.3, 78.2, 77.4, 56.3, 47.0, 39.8, 38.6, 37.9, 28.5, 27.6, 26.7, 25.8, 23.4, 21.6 (t, J$_{CF}$=2.0 Hz), 20.1, 17.8, 16.2, 14.5; HRMS (EI) calcd for C$_{35}$H$_{44}$O$_3$F$_2$ [M$^+$], 550.3259; found 550.3256.

The intermediate phosphonate 46 was prepared as follows.

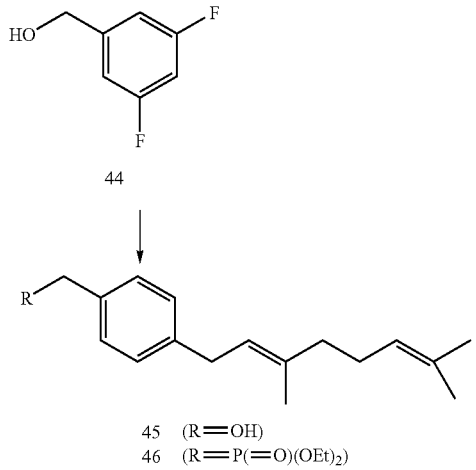

a. [4-(3,7-Dimethyl-octa-2,6-dienyl)-3,5-difluoro-phenyl]-methanol (45) A solution of benzylic alcohol 44 (67 mg, 0.46 mmol) and TMEDA (0.21 mL, 1.4 mmol) in THF (10 mL) was cooled to −20° C. After nBuLi (0.64 mL, 2.15 M in hexanes) was added dropwise and the solution was stirred at −20° C. for 1 h, CuBr as its DMS complex (192 mg, 0.93 mmol) was added in one portion and the solution was stirred for 1 h at −20° C. A solution of geranyl bromide (0.11 mL, 0.55 mmol) in THF (5 mL) was added to the reaction mixture via syringe at −20° C. and the solution was stirred for 2 h. The reaction was quenched by addition of 1N NH$_4$Cl, the aqueous layer was neutralized to pH 7 with 1N HCl, and then was extracted with EtOAc. The combined organic layers were washed with brine, dried (MgSO$_4$), and concentrated in vacuo. Purification by flash column chromatography (20% EtOAc in hexanes) afforded alcohol 45 (68 mg, 53%) as a clear oil: $^1$H NMR δ 6.91-6.83 (dm, J$_{HF}$=7.5 Hz, 2H), 5.23-5.19 (tm, J=7.3 Hz, 1H), 5.08-5.03 (tm, J=6.8 Hz, 1H), 4.65 (d, J=5.6 Hz, 2H, becomes a singlet at D$_2$O wash), 3.36 (d, J=7.2 Hz, 2H), 2.07-1.96 (m, 4H), 1.75 (s, 3H), 1.65 (s, 3H), 1.58 (s, 3H); $^{13}$C NMR δ 161.6 (dd, J$_{CF}$=246.9, 9.6 Hz, 2C), 141.2 (t, J$_{CF}$=9.0 Hz), 136.8, 131.7, 124.3, 120.7, 116.4 (t, J$_{CF}$=20.9 Hz), 109.4 (dd, J$_{CF}$=26.6, 8.9 Hz, 2C), 54.4 (t, J$_{CF}$=2.1 Hz), 39.8, 26.7, 25.9, 21.5 (t, J$_{CF}$=2.5 Hz), 17.9, 16.2; HRMS (EI) calcd for C$_{17}$H$_{22}$F$_2$O [M$^+$], 280.1639; found 280.1639.

b. [4-(3,7-Dimethyl-octa-2,6-dienyl)-3,5-difluoro-benzyl]-phosphonic acid diethyl ester (46) PBr$_3$ (0.03 mL, 0.32 mmol) was added dropwise to a solution of alcohol 45 (180 mg, 0.64 mmol) in ether (10 mL) and the solution was stirred for 7 h at 0° C. The reaction mixture was poured into ice water, extracted with ether, and washed with brine. The combined organic layer was dried (MgSO$_4$), and concentrated in vacuo. The resulting yellow oil was added to triethyl phosphite (3 mL) and sodium iodide (62 mg, 0.41 mmol), and the mixture was heated at 100° C. for 30 h. After this solution was allowed to cool to rt, it was poured into ether (10 mL) and washed with sodium thiosulfate. The mixture was extracted with ether, dried (MgSO$_4$), and concentrated in vacuo. The initial yellow oil was purified by flash chromatography (gradient, 30-80% EtOAc in hexanes) to afford phosphonate 46 (153 mg, 60%) as a light yellow oil: $^1$H NMR δ 6.84-6.77 (m, 2H), 5.22-5.17 (tm, J=6.4 Hz, 1H), 5.08-5.03 (tm, J=6.9 Hz, 1H), 4.11-4.00 (m, 4H), 3.35-3.32 (dm, J=7.2 Hz, 2H), 3.11-3.04 (dm, J$_{PH}$=21.7 Hz, 2H), 2.07-1.92 (m, 4H), 1.74 (s, 3H), 1.65 (s, 3H), 1.58 (s, 3H), 1.31-1.24 (tin, J=7.1 Hz, 6H); $^{13}$C NMR δ 161.4 (ddd, J$_{CF}$=245.7, 10.0 Hz, J$_{CP}$=3.5 Hz, 2C), 136.8, 132.0-131.6 (m), 131.7, 124.3, 120.7, 116.0 (td, J$_{CF}$=20.3 Hz, J$_{CP}$=3.5 Hz), 112.9-112.5 (m, 2C), 65.5 (d, J$_{CP}$=6.75 Hz, 2C), 39.8, 33.5 (dd, J$_{CP}$=139.2 Hz, J$_{CF}$=1.9 Hz), 26.7, 25.9, 21.4 (t, J$_{CF}$=1.7 Hz), 17.9, 16.6 (d, J$_{CP}$=6.00 Hz, 2C), 16.1; $^{31}$P NMR δ +24.8 (t, $J_{PF}$=2.3 Hz). Anal. Calcd for $C_{21}H_{31}F_2O_3P$: C, 62.99; H, 7.80. Found: C, 63.22; H, 7.98.

Example 5

5-Methoxy-1,1,4a-trimethyl-7-styryl-2,3,4,4a,9,9a-hexahydro-1H-xanthen-2-ol (59)

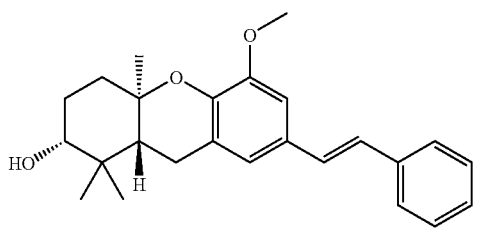

To a suspension of NaH (26 mg, 1 mmol) and 15C5 (5 mL, 3 mol %) in THF (5 mL) was added phosphonate 43 (25 mg, 0.12 mmol) and aldehyde 28 (15.8 mg, 0.05 mmol) at 0° C. and the reaction mixture was stirred for 10 h at rt. The reaction was quenched by addition of water and extracted with EtOAc. The combined organic layers were washed with brine, dried (MgSO$_4$), and concentrated in vacuo. Final purification of the residue by flash column chromatography (35% EtOAc in hexanes) afforded compound 59 (17 mg, 90%) as a clear oil: $^1$H NMR δ 7.50-7.47 (m, 2H), 7.37-7.34 (m, 2H), 7.26-7.20 (m, 1H), 6.98 (d, J=8.5 Hz, 2H), 6.91-6.87 (m, 2H), 3.90 (s, 3H), 3.46-3.41 (m, 1H), 2.77-2.75 (m, 1H), 2.72-2.68 (m, 2H), 2.16-2.11 (m, 1H), 1.90-1.81 (m, 2H), 1.74-1.55 (m, 3H), 1.26 (s, 3H), 1.11 (s, 3H), 0.89 (s, 3H); $^{13}$C NMR δ 149.2, 142.9, 137.9, 129.2, 128.9 (2C), 128.8, 127.4, 126.5, 126.4 (2C), 122.9, 120.8, 107.2, 78.2, 77.3, 56.3, 47.0, 38.6, 37.9, 28.5, 27.6, 23.4, 20.1, 14.5; HRMS (EI) calcd for $C_{25}H_{30}O_3$ [M$^+$], 378.2195; found 378.2195.

Example 6

5-[2-(7-Hydroxy-4-methoxy-8,8,10a-trimethyl-5,7,8,8a,9,10a-hexahydro-6H-xanthen-2-yl)-vinyl]-benzene-1,3-diol (60)

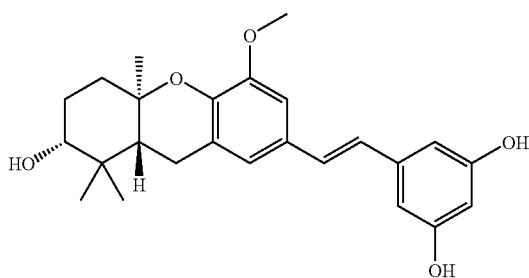

To a stirred solution of stilbene 54 (30 mg, 0.06 mmol) in methanol (5 mL) was added CSA (20 mg, 0.09 mmol) and the solution was allowed to stir 10 h at 50° C. The reaction mixture was allowed to cool to rt, concentrated in vacuo, and the residue was dissolved in EtOAc and water. The mixture was extracted with ether, washed with brine, dried (MgSO$_4$), and concentrated in vacuo. Final purification of the residue by flash column chromatography (60% EtOAc in hexanes) afforded compound 60 (23 mg, 93%) as a clear oil: $^1$H NMR (CDCl$_3$/CD$_3$OD) δ 7.06-6.88 (m, 4H), 6.58 (d, J=2.0 Hz, 2H), 6.31 (t, J=2.0 Hz, 1H), 3.97 (s, 3H), 3.75-3.68 (m, 1H), 2.96-2.81 (m, 2H), 2.20-1.68 (m, 5H), 1.33 (s, 3H), 1.16 (s, 3H), 0.97 (s, 3H); $^{13}$C NMR (CDCl$_3$/CD$_3$OD) δ 157.7 (2C), 148.3, 142.0, 139.4, 128.8, 128.0, 125.9, 122.3, 120.3, 106.6, 104.3 (2C), 101.2, 77.0, 76.7, 55.1, 46.9, 37.8, 37.2, 27.2, 26.2, 22.5, 18.9, 13.4; HRMS (EI) calcd for $C_{25}H_{30}O_5$ [M$^+$], 410.2093; found 410.2093.

The intermediate stilbene 54 was prepared as follows.

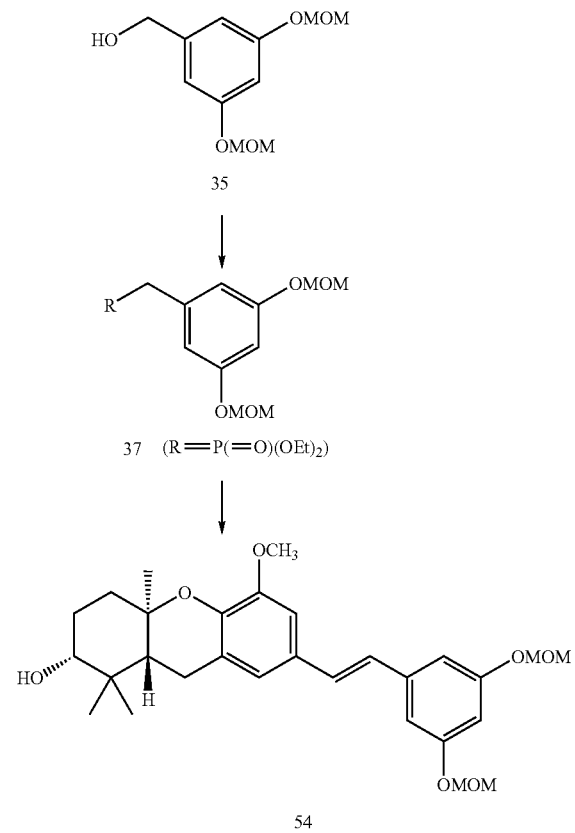

a. (3,5-bis-Methoxymethoxy-benzyl)-phosphonic acid diethyl ester (37). Methanesulfonyl chloride (1.4 mL, 18.1 mmol) was added dropwise to a stirred solution of alcohol 35 (881 mg, 3.9 mmol) and Et$_3$N (2.2 mL 15.76 mmol) in CH$_2$Cl$_2$ (150 mL). The solution was stirred for 2 h at 0° C. The reaction mixture was allowed to warm to rt over 5 h, quenched by addition of water, and extracted with EtOAc. The combined organic layers were washed with NH$_4$Cl (sat), brine, dried (MgSO$_4$), and concentrated in vacuo. The yellow residue was treated with NaI (2.33 g, 15.6 mmol) in acetone (20 mL) for 24 h at rt. The reaction mixture was concentrated in vacuo to a red solid, which was dissolved in EtOAc. After the resulting yellow solution was washed once with NaHCO$_3$ and then with Na$_2$S$_2$O$_3$ until the color faded, it was extracted with ether and the combined organic layers were dried (MgSO$_4$) and concentrated in vacuo. Final purification of the residue by flash column chromatography (30% EtOAc in hexanes) afforded compound iodide (1.12 g, 84%) as a yellow oil: $^1$H NMR δ 6.73 (d, J=2.2 Hz, 2H), 6.63 (t, J=2.2 Hz, 1H), 5.2 (s, 4H), 4.4 (s, 2H), 3.5 (s, 6H); $^{13}$C NMR δ 158.5 (2C), 141.5, 110.3 (2C), 104.7, 94.7 (2C), 56.3 (2C), 5.5; HRMS (EI) calcd for $C_{11}H_{15}O_4I$ [M⁺], 338.0015; found 338.0016. A stirred solution of this iodide (1.11 g, 3.3 mmol) in triethyl phosphite (2.5 mL) was heated at reflux for 9 h, then it was allowed to cool to rt and poured into ether (8 mL). The resulting mixture was extracted with ether, dried (MgSO₄) and concentrated in vacuo. Final purification of the residue by flash chromatography (gradient, 30-80% EtOAc in hexanes) afforded phosphonate 37 (734 mg, 64%) as a light yellow oil: $^1$H NMR δ 6.58-6.55 (m, 3H), 5.06 (s, 4H), 3.97 (m, 4H), 3.39 (s, 6H), 3.01 (d, $J_{PH}$=21.6 Hz, 2H), 1.20 (tm, J=7.1 Hz, 6H); $^{13}$C NMR δ 158.2 (d, $J_{CP}$=3.2 Hz, 2C), 133.8 (d, $J_{CP}$=8.8 Hz), 111.2 (d, $J_{CP}$=6.5 Hz, 2C), 103.5 (d, $J_{CP}$=3.4 Hz), 94.4 (2C), 62.1 (d, $J_{CP}$=6.6 Hz, 2C), 55.9 (2C), 33.9 (d, $J_{CP}$=138.1 Hz), 16.3 (d, $J_{CP}$=6.1 Hz, 2C); $^{31}$P NMR δ+25.7. Anal. Calcd for $C_{15}H_{25}O_7P$: C, 51.72; H, 7.23. Found: C, 51.55; H, 7.27.

b. 7-[2-(3,5-bis-Methoxymethoxy-phenyl)-vinyl]-5-methoxy-1,1,4a-trimethyl-2,3,4,4a,9,9a-hexahydro-1H-xanthen-2-ol (54) To a stirred suspension of NaH (30 mg, 1.3 mmol) and 15C5 (5 μL, 3 mol %) in THF (5 mL) was added phosphonate 37 (25 mg, 0.12 mmol) and aldehyde 28 (20 mg, 0.066 mmol) at 0° C. The reaction mixture was allowed to warm to rt over 10 h. The reaction was quenched by addition of water, and extracted with EtOAc. After the combined organic layers were washed with brine, dried (MgSO₄), and concentrated in vacuo, final purification by flash column chromatography (50% EtOAc in hexanes) afforded compound 54 (30 mg, 91%) as a clear oil: $^1$H NMR δ 7.00 (d, J=17.1 Hz, 1H), 6.90-6.85 (m, 5H), 6.64 (t, J=2.1 Hz, 1H), 5.20 (s, 4H), 3.90 (s, 3H), 3.51 (s, 6H), 3.46-3.42 (m, 1H), 2.76-2.74 (m, 1H), 2.73-2.71 (m, 1H), 2.17-2.11 (m, 1H), 1.91-1.81 (m, 2H), 1.75-1.54 (m, 2H), 1.27 (s, 3H), 1.12 (s, 3H), 0.90 (s, 3H); $^{13}$C NMR δ 158.7 (2C), 149.2, 143.0, 140.1, 129.6, 128.9, 126.2, 122.8, 120.9, 107.8 (2C), 107.3, 104.1, 94.7 (2C), 78.2, 77.3, 55.3 (2C), 56.2, 46.9, 38.6, 37.9, 28.5, 27.6, 23.4, 20.1, 14.5; HRMS (EI) calcd for $C_{29}H_{38}O_7$ [M⁺], 498.2618; found 498.2608. This compound is also a compound of the invention.

Example 7

2-(8-Hydroxy-3,7-dimethyl-octa-2,6-dienyl)-5-[2-(7-hydroxy-4-methoxy-8,8,10a-trimethyl-5,7,8,8a,9, 10a-hexahydro-6H-xanthen-2-yl)-vinyl]-benzene-1, 3-diol (62)

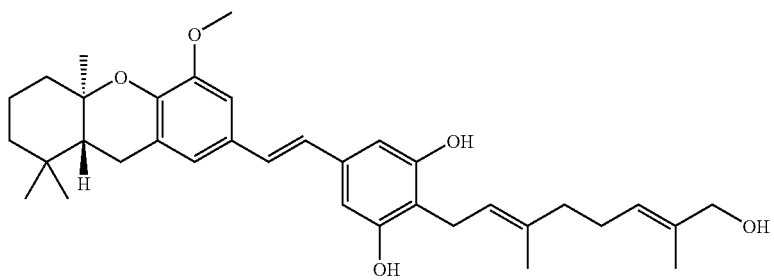

CSA (20 mg, 0.09 mmol) was added to a stirred solution of stilbene 58 (17 mg, 0.026 mmol) in methanol (5 mL) and the reaction mixture was allowed to stir for 15 h at 50° C. The reaction mixture was allowed to cool to rt, and concentrated in vacuo and the residue was dissolved in EtOAc and water. The mixture was extracted with ether, the organic layer was washed with brine, dried (MgSO₄), and concentrated in vacuo. Purification of the residue by flash column chromatography (80% EtOAc in hexanes) afforded compound 62 (6 mg, 42%) as a clear oil: $^1$H NMR δ 6.94-6.73 (m, 4H), 6.49 (s, 2H), 5.40 (s, 2H, exchangeable with D₂O), 5.31-5.29 (m, 2H), 4.01 (s, 2H), 3.89 (s, 3H), 3.45-3.43 (m, 3H), 2.74-2.72 (m, 1H), 2.72-2.70 (m, 1H), 2.37-2.12 (m, 5H), 1.91-1.57 (m, 10H), 1.46 (s, 1H, exchangeable with D₂O), 1.26 (s, 3H), 1.12 (s, 3H), 0.90 (s, 3H); $^{13}$C NMR δ 155.2 (2C), 149.2, 142.9, 139.2, 137.6, 136.5, 129.0 (2C), 125.8, 125.0, 122.9, 122.7, 120.8, 112.6, 107.2, 106.4 (2C), 78.1, 69.1, 56.2, 47.0, 39.4, 38.6, 37.9, 28.4, 27.6 (2C), 25.1, 23.4, 22.7, 20.1, 15.8, 14.5, 13.9; HRMS (EI) calcd for $C_{35}H_{46}O_6$ [M⁺], 561.3216; found 561.3214.

The intermediate stilbene 58 was prepared as follows.

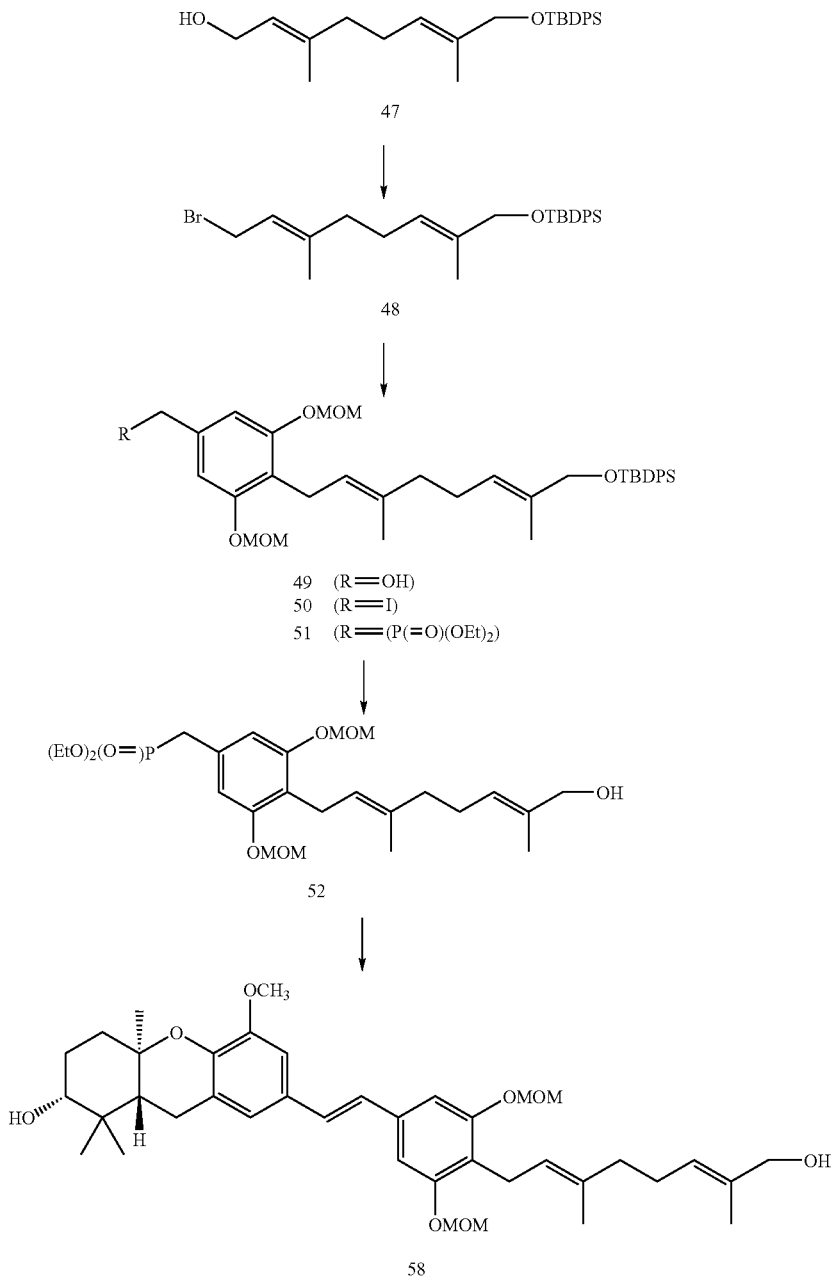

a. {4-[8-(tert-butyl-diphenyl-silanyloxy)-3,7-dimethyl-octa-2,6-dienyl]-3,5-bis-methoxymethoxy-phenyl}-methanol (49) PBr$_3$ (0.7 mL, 7.4 mmol) was added dropwise to a solution of alcohol 47 (521 mg, 1.27 mmol) in ether (10 mL) and the solution was stirred for 7 h at 0° C. The reaction mixture was poured into ice water, extracted with ether, and washed with brine. The combined organic layer was dried (MgSO$_4$), and concentrated in vacuo to give a yellow residue, bromide 48. A solution of benzylalcohol 35 (305 mg, 1.34 mmol) in THF (5 mL) was added to a stirred suspension of KH (87 mg, 2.2 mmol) in THF (10 mL) and the reaction mixture was stirred for 1 h at 0° C. After TMEDA (0.4 mL, 2.7 mmol) was added, the solution was cooled to −20° C., then nBuLi (1.87 mL, 2.15 M in hexanes) was added dropwise and the solution was stirred at −20° C. for 1 h. CuBr as its DMS complex (556 mg, 2.7 mmol) was added in one portion and the solution was stirred for 1 h at −20° C. Bromide 48 in THF (5 mL) was added to the reaction mixture via syringe at −20° C. After 2 h, the reaction was quenched by addition of 1N NH$_4$Cl, and the aqueous layer was neutralized to pH 7 with 1N HCl, and extracted with EtOAc. The combined organic layer was washed with brine, dried (MgSO$_4$), and concentrated in vacuo. Final purification by flash column chromatography (20% EtOAc in hexanes) afforded compound 49 (341 mg, 43% from alcohol 47) as a clear oil: $^1$H NMR δ 7.70-7.67 (m, 4H), 7.43-7.35 (m, 6H), 6.79 (s, 2H), 5.43-5.39 (tm, J=7.0 Hz, 1H), 5.26-5.19 (m, 5H), 4.62 (s, 2H), 4.03 (s, 2H), 3.47 (s, 6H), 3.40 (d, J=9 Hz, 2H), 2.19-1.96 (m, 4H), 1.81 (s, 3H), 1.59 (s, 3H), 1.06 (s, 9H); $^{13}$C NMR δ 156.0 (2C), 140.2, 135.8 (4C), 134.8, 134.2 (2C), 134.1, 129.7 (2C), 127.8 (4C), 124.6, 122.9, 119.6, 106.7 (2C), 94.6 (2C), 69.3, 65.7, 56.2 (2C), 39.8, 27.1 (3C), 26.4, 22.8, 19.5, 16.3, 13.7. Anal. Calcd for $C_{37}H_{50}O_6Si$: C, 71.81; H, 8.14. Found: C, 71.72; H, 7.98.

b. tert-Butyl-[8-(4-iodomethyl-2,6-bis-methoxymethoxy-phenyl)-2,6-dimethyl-octa-2,6-dienyloxy]-diphenyl-silane (50) Methanesulfonyl chloride (0.1 mL, 1.3 mmol) was added dropwise to a stirred solution of alcohol 49 (364 mg, 0.62 mmol) and Et$_3$N (0.2 mL 1.4 mmol) in CH$_2$Cl$_2$ (5 mL) and the solution was stirred for 2 h at 0° C. The reaction mixture was allowed to warm to rt over 5 h, quenched by addition of H$_2$O, and extracted with EtOAc. The combined organic layers were washed with NH$_4$Cl (sat) and brine, dried (MgSO$_4$), and concentrated in vacuo. The resulting yellow residue was allowed to react with NaI (132 mg, 0.886 mmol) in acetone (8 mL) for 24 h at rt. The reaction mixture was concentrated in vacuo to afford a red solid, which was dissolved in EtOAc. After the resulting yellow solution was washed once with NaHCO$_3$ and then with Na$_2$S$_2$O$_3$ until the color faded, it was extracted with ether and the combined organic layers were dried (MgSO$_4$) and concentrated in vacuo. Final purification by flash column chromatography (30% EtOAc in hexanes) afforded the iodide 50 (347 mg, 77%) as a yellow oil: $^1$H NMR δ 7.77-7.72 (m, 4H), 7.49-7.38 (m, 6H), 6.84 (s, 2H), 5.48-5.44 (tm, J=6.6 Hz, 1H), 5.29-5.19 (tm, J=6.0 Hz, 1H), 5.20 (s, 4H), 4.43 (s, 2H), 4.08 (s, 2H), 3.50 (s, 6H), 3.41 (d, J=7.1 Hz, 2H), 2.30-2.01 (m, 4H), 1.85 (s, 3H), 1.63 (s, 3H), 1.11 (s, 9H); $^{13}$C NMR δ 155.8 (2C), 138.1, 135.7 (4C), 134.9, 134.1 (2C), 134.0, 129.7 (2C), 127.8 (4C), 124.5, 122.6, 120.2, 108.6 (2C), 94.6 (2C), 69.6, 56.2 (2C), 39.8, 27.0 (3C), 26.3, 22.9, 19.5, 16.3, 13.7, 6.7; HRMS (EI) calcd for $C_{37}H_{49}IO_5Si$ [M$^+$], 728.2394; found 728.2395.

c. {4-[8-(tert-Butyl-diphenyl-silanyloxy)-3,7-dimethyl-octa-2,6-dienyl]-3,5-bis-methoxymethoxy-benzyl}-phosphonic acid diethyl ester (51) A solution of iodide 50 (68 mg, 0.093 mmol) and sodium iodide (39 mg, 0.26 mmol) in triethyl phosphite (1.5 mL) was heated at 100° C. for 20 h, allowed to cool to rt, and poured into ether (5 mL). The resulting mixture was extracted with ether, dried (MgSO$_4$), and concentrated in vacuo. The initial yellow oil was purified by flash chromatography (50% EtOAc in hexanes) to afford phosphonate 51 (63.5 mg, 92%) as light yellow oil: $^1$H NMR δ 7.70-7.67 (m, 4H), 7.42-7.34 (m, 6H), 6.70 (d, J$_{HP}$=2.3 Hz, 2H), 5.42-5.39 (tm, J=5.7 Hz, 1H), 5.21-5.17 (trm, J=7.0 Hz, 1H), 5.17 (s, 4H), 4.10-4.00 (m, 6H), 3.45 (s, 6H), 3.37 (d, J=7.0 Hz, 2H), 3.09 (d, J$_{PH}$=21.5 Hz, 2H), 2.14-1.95 (m, 4H), 1.80 (s, 3H), 1.58 (s, 3H), 1.28 (trm, J=7.08 Hz, 6H), 1.06 (s, 9H); $^{13}$C NMR δ 155.8 (d, J$_{CP}$=3.2 Hz, 2C), 135.8 (4C), 134.7, 134.1 (2C), 134.0, 130.5 (d, J$_{CP}$=9.0 Hz), 129.7 (2C), 127.7 (4C), 124.7, 123.0, 118.9 (d, J$_{CP}$=3.9 Hz), 108.8 (d, J$_{CP}$=6.6 Hz, 2C), 94.6 (2C), 69.2, 62.3 (d, J$_{CP}$=6.7 Hz, 2C), 56.2 (2C), 39.8, 34.1 (d, J$_{CP}$=138.3 Hz), 27.0 (3C), 26.5, 22.7, 19.5, 16.6 (d, J$_{CP}$=5.8 Hz, 2C), 16.3, 13.6; $^{31}$P NMR δ +26.2. Anal. Calcd for $C_{41}H_{59}O_8PSi$: C, 66.64; H, 8.05. Found: C, 66.58; H, 8.32.

d. [4-(8-Hydroxy-3,7-dimethyl-octa-2,6-dienyl)-3,5-bis-methoxymethoxy-benzyl]-phosphonic acid diethyl ester (52) TBAF (0.3 mL, 1M in THF, 0.3 mmol) was added to a solution of phosphonate 51 (55.1 mg, 0.075 mmol) in THF (3 mL) and the solution was stirred for 3 h at rt. The reaction was quenched by addition of water and EtOAc, and then extracted with EtOAc. The combined organic layer was washed with brine, dried (MgSO$_4$), and concentrated in vacuo. Final purification of the residue by flash column chromatography (gradient, 60-100% EtOAc in hexanes) afforded compound 52 (36 mg, 96%) as a clear oil: $^1$H NMR δ 6.66 (broad s, 2H), 5.30-5.24 (m, 1H), 5.13-5.06 (m, 5H), 4.04-3.97 (m, 4H), 3.83 (s, 2H), 3.42 (s, 6H), 3.32 (d, J=7.0 Hz, 2H), 3.04 (d, J$_{PH}$=21.5 Hz, 2H), 2.07-1.95 (m, 4H), 1.73 (s, 3H), 1.53 (s, 3H), 1.24 (trm, J=6.8 Hz, 6H); $^{13}$C NMR δ 155.8 (d, J$_{CP}$=3.4 Hz, 2C), 135.1, 134.1, 130.4 (d, J$_{CP}$=9.1 Hz), 125.9, 123.4, 119.1 (d, J$_{CP}$=3.9 Hz), 109.9 (d, J$_{CP}$=6.6 Hz, 2C), 94.7 (2C), 68.9, 62.3 (d, J$_{CP}$=6.7 Hz, 2C), 56.2 (2C), 39.5, 34.0 (d, J$_{CP}$=138.3 Hz), 26.1, 22.7, 16.6 (d, J$_{CP}$=6.1 Hz, 2C), 16.2, 13.8; $^{31}$P NMR δ +26.2; HRMS (EI) calcd for $C_{25}H_{14}O_8P$ [M$^+$], 500.2539; found 500.2531.

e. 7-{2-[4-(8-Hydroxy-3,7-dimethyl-octa-2,6-dienyl)-3,5-bis methoxymethoxy-phenyl]-vinyl}-5-methoxy-1,1,4a-trimethyl-2,3,4,4a,9,9a-hexahydro-1H-xanthen-2-ol (58) To a suspension of NaH (12 mg, 0.3 mmol) and 15C5 (5 mL, 3 mol %) in THF (5 mL) was added phosphonate 52 (34 mg, 0.068 mmol) and aldehyde 28 (16 mg, 0.053 mmol) at 0° C. and the reaction mixture was allowed to warm to rt over 10 h. The reaction was quenched by addition of water and extracted with EtOAc. The combined organic layers were washed with brine, dried (MgSO$_4$), and concentrated in vacuo. Purification of the resulting oil by flash column chromatography (50% EtOAc in hexanes) afforded compound 58 (20.5 mg, 60%) as a clear oil: $^1$H NMR δ 6.99-6.87 (m, 6H), 5.37-5.33 (tm, J=6.0 Hz, 1H), 5.24-5.18 (m, 5H), 3.95 (s, 2H), 3.91 (s, 3H), 3.52-3.39 (m, 9H), 2.74-2.72 (m, 1H), 2.72-2.70 (m, 1H), 2.17-1.98 (m, 5H), 1.90-1.57 (m, 10H), 1.26 (s, 3H), 1.12 (s, 3H), 0.90 (s, 3H); $^{13}$C NMR δ 156.1 (2C), 149.2, 142.8, 137.0, 134.9, 134.4, 129.1, 128.6, 126.6, 126.2, 123.3, 122.8, 120.8, 119.7, 107.1, 106.3 (2C), 94.8 (2C), 78.3, 77.4, 69.2, 56.2 (2C), 47.0, 39.6, 38.6, 37.9, 28.5, 27.6, 26.3, 23.4, 22.9, 20.1, 16.3, 14.5, 14.3, 13.9; HRMS (EI) calcd for $C_{39}H_{54}O_8$ [M$^+$], 650.3819; found 650.3812. This compound is also a compound of the invention.

Example 8

7-[2-(3-Hydroxy-phenyl)-vinyl]-5-methoxy-1,1,4a-trimethyl-2,3,4,4a,9,9a-hexahydro-1H-xanthen-2-ol (61)

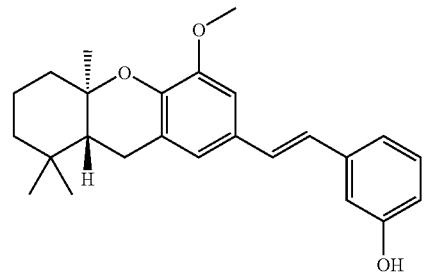

CSA (17 mg, 0.073 mmol) was added to a stirred solution of stilbene 55 (16 mg, 0.036 mmol) in methanol (5 mL) and the reaction mixture was allowed to stir for 15 h at rt. The reaction mixture was concentrated in vacuo and the residue was dissolved in EtOAc and water. The mixture was extracted with ether, the organic layer was washed with brine, dried (MgSO$_4$), and concentrated in vacuo. Purification of the residue by flash column chromatography (60% EtOAc in hexanes) afforded compound 61 (9 mg, 63%) as a clear oil: $^1$H NMR δ 7.26-7.19 (m, 1H), 7.06-6.85 (m, 6H), 6.73-6.70 (m, 1H), 5.05 (s, 1H, exchangeable with D$_2$O), 3.83 (s, 3H), 3.46-3.43 (m, 1H), 2.75-2.66 (m, 2H), 2.18-1.61 (m, 5H), 1.49 (br. s, 1H, exchangeable with D$_2$O), 1.26 (s, 3H), 1.11 (s, 3H), 0.89 (s, 3H); $^{13}$C NMR δ 156.1, 149.2, 142.9, 139.6, 130.0, 129.4, 129.0, 126.1, 122.9, 120.9, 119.3, 114.4, 112.9, 107.2, 78.3, 77.4, 56.2, 46.9, 38.6, 37.8, 28.5, 27.6, 23.4, 20.1, 14.5; HRMS (EI) calcd for C$_{25}$H$_{30}$O$_4$ (M+H$^+$), 395.2222; found 395.2237.

The intermediate stilbene 55 was prepared as follows.

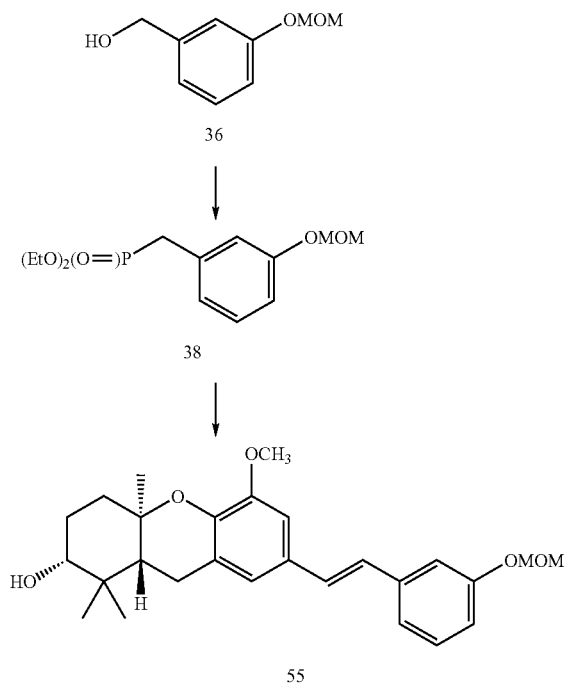

a. (3-Methoxymethoxy-benzyl)-phosphonic acid diethyl ester (38) Methanesulfonyl chloride (1.0 mL, 12.9 mmol) was added dropwise to a solution of alcohol 36 (500 mg, 2.97 mmol) and Et$_3$N (0.5 mL 3.6 mmol) in CH$_2$Cl$_2$ (10 mL) and the solution was stirred for 2 h at 0° C. The reaction mixture was allowed to warm to rt over 5 h, quenched by addition of H$_2$O, and extracted with EtOAc. The combined organic layers were washed with NH$_4$Cl (sat), brine, dried (MgSO$_4$), and concentrated in vacuo. The resulting yellow residue was treated with NaI (1 g, 3.6 mmol) in acetone (15 mL) for 24 h at rt. This reaction mixture was concentrated in vacuo to afford a red solid, which was dissolved in EtOAc. After the resulting yellow solution was washed once with NaHCO$_3$ and then with Na$_2$S$_2$O$_3$ until the color faded, it was extracted with ether and the combined organic layers were dried (MgSO$_4$) and concentrated in vacuo. The resulting yellow oil was added to triethyl phosphite (4 mL) and the solution was heated at 100° C. for 20 h. After the solution was allowed to cool to rt, it was poured into ether (10 mL). The mixture was extracted with ether, dried (MgSO$_4$), and concentrated in vacuo. The initial yellow oil was purified by flash chromatography (50% EtOAc in hexanes) to afford phosphonate 38 (709 mg, 83%) as a light yellow oil: $^1$H NMR δ 7.20 (tr, J=7.9 Hz, 1H), 7.08-6.89 (m, 3H), 5.17 (s, 2H), 4.15-3.97 (m, 4H), 3.44 (s, 3H), 3.11 (d, J$_{PH}$=21.6 Hz, 2H), 1.27-1.22 (m, 6H); $^{13}$C NMR δ 157.1 (d, J$_{CP}$=3.2 Hz), 132.9 (d, J$_{CP}$=8.9 Hz), 129.2 (d, J$_{CP}$=3.1 Hz), 123.1 (d, J$_{CP}$=6.5 Hz), 117.5 (d, J$_{CP}$=6.5 Hz), 114.5 (d, J$_{CP}$=3.5 Hz), 94.1, 61.8 (d, J$_{CP}$=6.7 Hz, 2C), 55.6, 33.4 (d, J$_{CP}$=137.2 Hz), 16.1 (d, J$_{CP}$=6.0 Hz, 2C); $^{31}$P NMR δ +25.8. Anal. Calcd for C$_{13}$H$_{21}$O$_5$P: C, 54.16; H, 7.34. Found: C, 53.98; H, 7.35.

b. 5-Methoxy-7-[2-(3-methoxymethoxy-phenyl)-vinyl]-1,1,4a-trimethyl-2,3,4,4a,9,9a-hexahydro-1H-xanthen-2-ol (55). To a stirred suspension of NaH (27 mg, 0.68 mmol) and 15C5 (5 μL, 3 mol %) in THF was added phosphonate 38 (50 mg, 0.173 mmol) and aldehyde 28 (20 mg, 0.066 mmol) at 0° C. and the reaction mixture was allowed to warm to rt over 10 h. The reaction was quenched by addition of water and extracted with EtOAc. The combined organic layers were washed with brine, dried (MgSO$_4$), and concentrated in vacuo. Final purification of the residue by flash column chromatography (50% EtOAc in hexanes) afforded compound 55 (18 mg, 62%) as a clear oil: $^1$H NMR δ 7.29-6.87 (m, 8H), 5.21 (s, 2H), 3.90 (s, 3H), 3.51 (s, 3H), 3.46-3.39 (m, 1H), 2.74-2.72 (m, 2H), 2.16-1.59 (m, 5H), 1.26 (s, 3H), 1.11 (s, 3H), 0.89 (s, 3H) $^{13}$C NMR δ 157.8, 149.2, 142.9, 139.5, 129.8, 129.3, 129.0, 126.3, 122.9, 120.9, 120.3, 115.3, 113.9, 107.2, 94.7, 78.2, 77.3, 56.3, 46.9, 38.6, 37.9, 29.9, 28.5, 27.6, 23.4, 20.1, 14.5; HRMS (ES+) calcd for C$_{27}$H$_{34}$O$_5$ (M+H)$^+$, 439.2484; found 439.2475. This compound is also a compound of the invention.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:
1. A pharmaceutical composition comprising a compound of formula (XX):

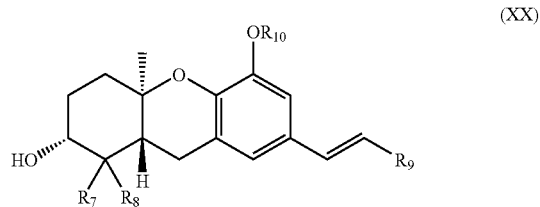

wherein:
R$_7$ and R$_8$ are each independently H or (C$_1$-C$_6$)alkyl;
R$_9$ is H, (C$_1$-C$_{15}$)alkenyl, (C$_2$-C$_{15}$)alkynyl, (C$_2$-C$_{15}$) alkoxy, (C$_{1-15}$) alkanoyl, (C$_1$-C$_{15}$)alkoxycarbonyl, (C$_2$-C$_{15}$)alkanoyloxy, aryl or heteroaryl, which aryl or heteroaryl is optionally substituted with one or more halo, hydroxy, cyano, CF$_3$, OCF$_3$, NR$^a$R$^b$, (C$_1$-C$_{15}$)alkyl, (C$_2$-C$_{15}$)alkenyl, (C$_2$-C$_{15}$)alkynyl, (C$_1$-C$_{15}$)alkoxy, (C$_1$-C$_{15}$)alkanoyl, (C$_1$-C$_{15}$)alkoxycarbonyl, (C$_1$-C$_{15}$)alkoxy (C$_1$-C$_{15}$)alkoxy,—P(=O)(OH)$_2$, and (C$_2$-C$_{15}$)alkanoyloxy;
R$_{10}$ is H or (C$_1$-C$_6$) alkyl; and
R$^a$ and R$^b$ are each independently H or (C$_1$-C$_6$)alkyl
wherein any (C$_1$-C$_{15}$)alkyl, (C$_2$-C$_{15}$)alkenyl, (C$_2$-C$_{15}$) alkynyl, (C$_1$-C$_{15}$)alkoxy, (C$_1$-C$_{15}$) alkanoyl, (C$_1$-C$_{15}$) alkoxycarbonyl, or (C$_2$-C$_{15}$)alkanoyloxy of R$_7$, R$_8$ and $R_9$ is optionally substituted with one or more halo, hydroxy, cyano, or oxo (=O)

or a pharmaceutically acceptable salt thereof;

and a pharmaceutically acceptable carrier.

2. A method for treating cancer comprising administering a therapeutically effective amount of a compound of formula (XX):

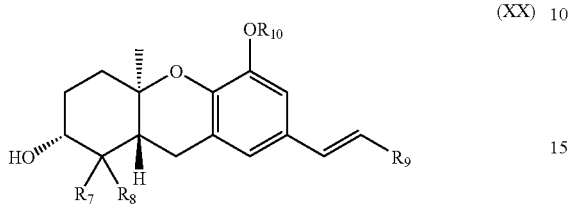

(XX)

wherein:

$R_7$ and $R_8$ are each independently H or $(C_1-C_6)$alkyl;

$R_9$ is H, $(C_1-C_{15})$alkenyl, $(C_2-C_{15})$alkynyl, $(C_1-C_{15})$alkoxy, $(C_{1-15})$ alkanoyl, $(C_1-C_{15})$alkoxycarbonyl, $(C_2-C_{15})$alkanoyloxy, aryl or heteroaryl, which aryl or heteroaryl is optionally substituted with one or more halo, hydroxy, cyano, $CF_3$, $OCF_3$, $NR^aR^b$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, $(C_1-C_{15})$alkoxy $(C_1-C_{15})$alkoxy, —P(=O)(OH)$_2$, and $(C_2-C_{15})$alkanoyloxy;

$R_{10}$ is H or $(C_1-C_6)$ alkyl; and $R^a$ and $R^b$ are each independently H or $(C_1-C_6)$alkyl wherein any $(C_1-C_{15})$alkyl, $(C_2-C_{15})$alkenyl, $(C_2-C_{15})$alkynyl, $(C_1-C_{15})$alkoxy, $(C_1-C_{15})$ alkanoyl, $(C_1-C_{15})$alkoxycarbonyl, or $(C_2-C_{15})$alkanoyloxy of $R_7$, $R_8$ and $R_9$ is optionally substituted with one or more halo, hydroxy, cyano, or oxo (=O)

or a pharmaceutically acceptable salt thereof;

to a mammal.

3. The method of claim 2 wherein the cancer is breast cancer or a cancer of the CNS or renal system.

4. The composition of claim 1 wherein $R_7$ is H.

5. The composition of claim 1 wherein $R_7$ is $(C_1-C_6)$ alkyl.

6. The composition of claim 1 wherein $R_8$ is H.

7. The composition of claim 1 wherein $R_8$ is $(C_1-C_6)$ alkyl.

8. The composition of claim 1 wherein $R_9$ is H.

9. The composition of claim 1 wherein $R_9$ is $(C_1-C_{15})$alkyl, $(C_2-C_{15})$alkenyl, $(C_2-C_{15})$ alkynyl, $(C_1-C_{15})$alkoxy, $(C_1-C_{15})$alkanoyl, $(C_1-C_{15})$alkoxycarbonyl, $(C_2-C_{15})$alkanoyloxy.

10. The composition of claim 1 wherein $R_9$ is aryl optionally substituted with one or more halo, hydroxy, cyano, $CF_3$, $OCF_3$, $NR^aR^b$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, and $(C_2-C_{15})$alkanoyloxy.

11. The composition of claim 1 wherein $R_9$ is of the formula

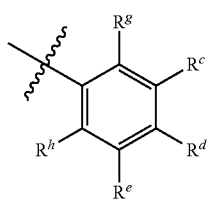

wherein:

$R^c$ and $R^e$ are each independently H, halo, hydroxy, $(C_1-C_{15})$alkyl, $(C_2-C_{15})$alkenyl, $(C_2-C_{15})$ alkynyl, $(C_1-C_{15})$alkoxy, methoxymethoxy, and $(C_2-C_{15})$alkanoyloxy; and $R^d$ is H, $(C_1-C_{15})$alkyl, $(C_2-C_{15})$alkenyl, $(C_2-C_{15})$alkynyl, $(C_1-C_{15})$alkoxy, $(C_1-C_{15})$ alkanoyl, $(C_1-C_{15})$alkoxycarbonyl, and $(C_2-C_{15})$alkanoyloxy;

$R^g$ is H, cyano, fluoro, or —P(=O)(OH)$_2$; and $R^h$ is H, cyano, fluoro, or —P(=O)(OH)$_2$;

wherein any $(C_1-C_{15})$alkyl, $(C_2-C_{15})$alkenyl, $(C_2-C_{15})$ alkynyl, $(C_1-C_{15})$alkoxy, $(C_1-C_{15})$ alkanoyl, $(C_1-C_{15})$alkoxycarbonyl, or $(C_2-C_{15})$alkanoyloxy of $R^c$, $R^e$, and $R^d$ is optionally substituted with one or more halo, hydroxy, cyano, or oxo (=O).

12. The composition of claim 1 wherein $R_9$ is isoxazolyl, imidazolyl, pyridyl, indolyl, or benzo[b]furanyl.

13. The method of claim 2 wherein $R_7$ is H.

14. The method of claim 2 wherein $R_7$ is $(C_1-C_6)$ alkyl.

15. The method of claim 2 wherein $R_8$ is H.

16. The method of claim 2 wherein $R_8$ is $(C_1-C_6)$ alkyl.

17. The method of claim 2 wherein $R_9$ is H.

18. The method of claim 2 wherein $R_9$ is $(C_1-C_{15})$alkyl, $(C_2-C_{15})$alkenyl, $(C_2-C_{15})$ alkynyl, $(C_1-C_{15})$alkoxy, $(C_1-C_{15})$ alkanoyl, $(C_1-C_{15})$alkoxycarbonyl, $(C_2-C_{15})$alkanoyloxy.

19. The method of claim 2 wherein $R_9$ is aryl optionally substituted with one or more halo, hydroxy, cyano, $CF_3$, $OCF_3$, $NR^aR^b$, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, and $(C_2-C_{15})$alkanoyloxy.

20. The method of claim 2 wherein $R_9$ is of the formula

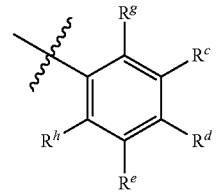

wherein:

$R^c$ and $R^e$ are each independently H, halo, hydroxy, $(C_1-C_{15})$alkyl, $(C_2-C_{15})$alkenyl, $(C_2-C_{15})$ alkynyl, $(C_1-C_{15})$alkoxy, methoxymethoxy, and $(C_2-C_{15})$alkanoyloxy; and $R^d$ is H, $(C_1-C_{15})$alkyl, $(C_2-C_{15})$alkenyl, $(C_2-C_{15})$alkynyl, $(C_1-C_{15})$alkoxy, $(C_1-C_{15})$ alkanoyl, $(C_1-C_{15})$alkoxycarbonyl, and $(C_2-C_{15})$alkanoyloxy;

$R^g$ is H, cyano, fluoro, or —P(=O)(OH)$_2$; and $R^h$ is H, cyano, fluoro, or —P(=O)(OH)$_2$;

wherein any $(C_1-C_{15})$alkyl, $(C_2-C_{15})$alkenyl, $(C_2-C_{15})$ alkynyl, $(C_1-C_{15})$alkoxy, $(C_1-C_{15})$ alkanoyl, $(C_1-C_{15})$alkoxycarbonyl, or $(C_2-C_{15})$alkanoyloxy of $R^c$, $R^e$, and $R^d$ is optionally substituted with one or more halo, hydroxy, cyano, or oxo (=O).

21. The method of claim 2 wherein $R_9$ is isoxazolyl, imidazolyl, pyridyl, indolyl, or benzo [b]furanyl.

* * * * *

UNITED STATES PATENT AND TRADEMARK OFFICE
CERTIFICATE OF CORRECTION

PATENT NO. : 7,902,228 B2
APPLICATION NO. : 12/025617
DATED : March 8, 2011
INVENTOR(S) : David F. Wiemer Page 1 of 1

It is certified that error appears in the above-identified patent and that said Letters Patent is hereby corrected as shown below:

Claim 1, Col. 42, line 54
Replace
$R_9$ is H, $(C_1-C_{15})$alkenyl, $(C_2-C_{15})$alkynyl, $(C_2-C_{15})$
With
$R_9$ is H, $(C_1-C_{15})$alkyl, $(C_2-C_{15})$alkenyl, $(C_2-C_{15})$alkynyl, $(C_1-C_{15})$ Claim 2, Col. 43, line 21
Replace
$R_9$ is H, $(C_1-C_{15})$alkenyl, $(C_2-C_{15})$alkynyl,
With
$R_9$ is H, $(C_1-C_{15})$alkyl, $(C_2-C_{15})$alkenyl, $(C_2-C_{15})$alkynyl, Claim 19, Col. 44, line 31
Replace
$(C_1C_{15})$alkyl
With
$(C_1-C_{15})$alkyl Signed and Sealed this
Thirty-first Day of January, 2012

David J. Kappos
*Director of the United States Patent and Trademark Office*